United States Patent
Geusen et al.

(10) Patent No.: US 9,233,015 B2
(45) Date of Patent: Jan. 12, 2016

(54) ENDOVASCULAR DELIVERY SYSTEM WITH AN IMPROVED RADIOPAQUE MARKER SCHEME

(71) Applicant: TriVascular, Inc., Santa Rosa, CA (US)

(72) Inventors: Mark Geusen, Santa Rosa, CA (US); Michael V. Chobotov, Santa Rosa, CA (US)

(73) Assignee: TRIVASCULAR, INC., Santa Rosa, CA (US)

( * ) Notice: Subject to any disclaimer, the term of this patent is extended or adjusted under 35 U.S.C. 154(b) by 243 days.

(21) Appl. No.: 13/803,050

(22) Filed: Mar. 14, 2013

(65) Prior Publication Data

US 2013/0338752 A1 Dec. 19, 2013

Related U.S. Application Data

(60) Provisional application No. 61/660,413, filed on Jun. 15, 2012.

(51) Int. Cl.
*A61F 2/95* (2013.01)
*A61F 2/966* (2013.01)

(52) U.S. Cl.
CPC . *A61F 2/95* (2013.01); *A61F 2/966* (2013.01); *A61F 2002/9511* (2013.01); *A61F 2002/9665* (2013.01); *A61F 2250/0003* (2013.01); *A61F 2250/0098* (2013.01)

(58) Field of Classification Search
CPC . A61F 2/962; A61F 2/966; A61F 2002/9505; A61F 2002/8511; A61F 2002/9665; A61F 2250/0098; A61F 2002/9511
USPC ..................... 623/1.11, 1.12, 2.11
See application file for complete search history.

(56) References Cited

U.S. PATENT DOCUMENTS

| | | | |
|---|---|---|---|
| 4,041,931 A | 8/1977 | Elliott et al. |
| 4,202,349 A | 5/1980 | Jones |
| 4,616,652 A | 10/1986 | Simpson |
| 4,762,128 A | 8/1988 | Rosenbluth |
| 4,781,681 A | 11/1988 | Sharrow et al. |
| 4,793,359 A | 12/1988 | Sharrow |
| 4,796,637 A | 1/1989 | Mascuch et al. |
| 4,830,003 A | 5/1989 | Wolff et al. |
| 4,917,088 A | 4/1990 | Crittenden |
| 4,928,693 A | 5/1990 | Goodin et al. |
| 4,976,690 A | 12/1990 | Solar et al. |

(Continued)

FOREIGN PATENT DOCUMENTS

| | | |
|---|---|---|
| EP | 0637454 A1 | 8/1995 |
| EP | 1880695 A1 | 1/2008 |
| EP | 2208483 A1 | 7/2010 |

OTHER PUBLICATIONS

English translation of EP1880695(A1), Jan. 23, 2008.

(Continued)

*Primary Examiner* — Kathleen Holwerda
(74) *Attorney, Agent, or Firm* — Hoffman & Baron, LLP

(57) ABSTRACT

An endovascular delivery system for an endovascular prosthesis includes a radiopaque marker system for accurate delivery of the prosthesis. The radiopaque marker system is disposed within a prosthesis or stent holder within the delivery system. The radiopaque marker system includes a plurality of radiopaque markers that provide different views rotation of the prosthesis or stent holder.

17 Claims, 20 Drawing Sheets

(56) References Cited

U.S. PATENT DOCUMENTS

| | | | |
|---|---|---|---|
| 5,007,434 A | 4/1991 | Doyle et al. |
| 5,015,230 A | 5/1991 | Martin et al. |
| 5,034,005 A | 7/1991 | Appling |
| 5,102,390 A | 4/1992 | Crittenden et al. |
| 5,158,084 A | 10/1992 | Ghiatas |
| 5,174,302 A | 12/1992 | Palmer |
| 5,203,777 A | 4/1993 | Lee |
| 5,209,730 A | 5/1993 | Sullivan |
| 5,209,749 A | 5/1993 | Buelna |
| 5,226,889 A | 7/1993 | Sheiban |
| 5,246,420 A | 9/1993 | Kraus et al. |
| 5,253,653 A | 10/1993 | Daigle et al. |
| 5,261,878 A | 11/1993 | Galindo |
| 5,263,928 A | 11/1993 | Trauthen et al. |
| 5,275,622 A * | 1/1994 | Lazarus et al. ............... 623/1.11 |
| 5,318,032 A | 6/1994 | Lonsbury et al. |
| 5,318,529 A | 6/1994 | Kontos |
| 5,318,535 A | 6/1994 | Miraki |
| 5,353,808 A | 10/1994 | Viera |
| 5,364,354 A | 11/1994 | Walker et al. |
| 5,395,332 A | 3/1995 | Ressemann et al. |
| 5,406,960 A | 4/1995 | Corso, Jr. |
| 5,413,557 A | 5/1995 | Solar |
| 5,429,597 A | 7/1995 | Demello et al. |
| 5,429,605 A | 7/1995 | Richling et al. |
| 5,452,726 A | 9/1995 | Burmeister et al. |
| 5,458,615 A | 10/1995 | Klemm et al. |
| 5,474,537 A | 12/1995 | Solar |
| 5,476,100 A | 12/1995 | Galel |
| 5,479,938 A | 1/1996 | Weier |
| 5,489,295 A | 2/1996 | Piplani et al. |
| 5,549,552 A | 8/1996 | Peters et al. |
| 5,558,652 A | 9/1996 | Henke |
| 5,562,725 A | 10/1996 | Schmitt et al. |
| 5,562,728 A | 10/1996 | Lazarus et al. |
| 5,569,199 A | 10/1996 | Solar |
| 5,571,086 A | 11/1996 | Kaplan et al. |
| 5,632,771 A | 5/1997 | Boatman et al. |
| 5,634,928 A | 6/1997 | Fischell et al. |
| 5,645,532 A | 7/1997 | Horgan |
| 5,669,880 A | 9/1997 | Solar |
| 5,676,146 A | 10/1997 | Scarborough |
| 5,683,451 A | 11/1997 | Lenker et al. |
| 5,690,642 A | 11/1997 | Osborne et al. |
| 5,707,376 A | 1/1998 | Kavteladze et al. |
| 5,713,913 A | 2/1998 | Lary et al. |
| 5,741,327 A | 4/1998 | Frantzen |
| 5,743,874 A | 4/1998 | Fischell et al. |
| 5,759,174 A | 6/1998 | Fischell et al. |
| 5,779,731 A | 7/1998 | Leavitt |
| 5,782,810 A | 7/1998 | O'Donnell |
| 5,836,892 A | 11/1998 | Lorenzo |
| 5,843,090 A | 12/1998 | Schuetz |
| 5,860,923 A | 1/1999 | Lenker et al. |
| RE36,104 E | 2/1999 | Solar |
| 5,916,263 A | 6/1999 | Goicoechea et al. |
| 5,944,712 A | 8/1999 | Frassica et al. |
| 5,947,977 A | 9/1999 | Slepian et al. |
| 5,948,489 A | 9/1999 | Hopkins |
| 5,968,052 A | 10/1999 | Sullivan, III et al. |
| 5,976,153 A | 11/1999 | Fischell et al. |
| 5,980,531 A | 11/1999 | Goodin et al. |
| 6,004,328 A | 12/1999 | Solar |
| 6,022,374 A | 2/2000 | Imran |
| 6,053,913 A | 4/2000 | Tu et al. |
| 6,078,832 A | 6/2000 | Lenker et al. |
| 6,165,213 A | 12/2000 | Goicoechea et al. |
| 6,174,330 B1 | 1/2001 | Stinson |
| 6,210,396 B1 | 4/2001 | MacDonald et al. |
| 6,214,038 B1 | 4/2001 | Piplani et al. |
| 6,235,050 B1 | 5/2001 | Quiachon et al. |
| 6,240,231 B1 | 5/2001 | Ferrera et al. |
| 6,241,759 B1 | 6/2001 | Piplani et al. |
| 6,251,132 B1 * | 6/2001 | Ravenscroft et al. ........ 623/1.11 |
| 6,251,135 B1 | 6/2001 | Stinson et al. |
| 6,285,903 B1 | 9/2001 | Rosenthal et al. |
| 6,293,966 B1 | 9/2001 | Frantzen |
| 6,302,906 B1 | 10/2001 | Goicoechea et al. |
| 6,306,162 B1 | 10/2001 | Patel |
| 6,331,188 B1 | 12/2001 | Lau et al. |
| 6,340,367 B1 | 1/2002 | Stinson et al. |
| 6,355,060 B1 | 3/2002 | Lenker et al. |
| 6,361,557 B1 | 3/2002 | Gittings et al. |
| 6,368,345 B1 | 4/2002 | Dehdashtian et al. |
| 6,371,928 B1 | 4/2002 | Mcfann et al. |
| 6,402,777 B1 | 6/2002 | Globerman et al. |
| 6,409,752 B1 | 6/2002 | Boatman et al. |
| 6,428,512 B1 | 8/2002 | Anderson et al. |
| 6,432,130 B1 | 8/2002 | Hanson |
| 6,443,979 B1 | 9/2002 | Stalker et al. |
| 6,451,053 B1 | 9/2002 | Dehdashtian et al. |
| 6,457,365 B1 | 10/2002 | Stephens et al. |
| 6,464,720 B2 | 10/2002 | Boatman et al. |
| 6,520,934 B1 | 2/2003 | Lee et al. |
| 6,520,984 B1 | 2/2003 | Garrison et al. |
| 6,524,335 B1 | 2/2003 | Hartley et al. |
| 6,540,721 B1 | 4/2003 | Voyles et al. |
| 6,599,316 B2 | 7/2003 | Vardi et al. |
| 6,613,075 B1 | 9/2003 | Healy et al. |
| 6,626,936 B2 | 9/2003 | Stinson |
| 6,656,212 B2 | 12/2003 | Ravenscroft et al. |
| 6,692,483 B2 | 2/2004 | Vardi et al. |
| 6,702,802 B1 | 3/2004 | Hancock et al. |
| 6,761,708 B1 | 7/2004 | Chiu et al. |
| 6,786,918 B1 | 9/2004 | Krivoruchko et al. |
| 6,814,746 B2 | 11/2004 | Thompson et al. |
| 6,818,013 B2 | 11/2004 | Mitelberg et al. |
| 6,858,034 B1 | 2/2005 | Hijlkema et al. |
| 6,918,928 B2 | 7/2005 | Wolinsky et al. |
| 6,945,989 B1 | 9/2005 | Betelia et al. |
| 6,951,554 B2 | 10/2005 | Johansen et al. |
| 6,955,685 B2 | 10/2005 | Escamilla et al. |
| 6,962,602 B2 | 11/2005 | Vardi et al. |
| 6,999,809 B2 | 2/2006 | Currier et al. |
| 7,004,964 B2 | 2/2006 | Thompson et al. |
| 7,025,716 B1 | 4/2006 | Meloul et al. |
| 7,033,325 B1 | 4/2006 | Sullivan |
| 7,037,331 B2 | 5/2006 | Mitelberg et al. |
| 7,083,641 B2 | 8/2006 | Stinson et al. |
| 7,083,822 B2 | 8/2006 | Brightbill |
| 7,105,015 B2 | 9/2006 | Goshgarian |
| 7,175,654 B2 | 2/2007 | Bonsignore et al. |
| 7,208,002 B2 | 4/2007 | Shelso |
| 7,208,008 B2 | 4/2007 | Clarke |
| 7,235,083 B1 | 6/2007 | Perez et al. |
| 7,243,408 B2 | 7/2007 | Vietmeier et al. |
| 7,252,679 B2 | 8/2007 | Fischell et al. |
| 7,303,580 B2 | 12/2007 | Parker |
| 7,303,798 B2 | 12/2007 | Bavaro et al. |
| 7,309,351 B2 | 12/2007 | Escamilla et al. |
| 7,320,702 B2 | 1/2008 | Hammersmark et al. |
| 7,331,985 B2 | 2/2008 | Thompson et al. |
| 7,462,192 B2 | 12/2008 | Norton et al. |
| 7,485,139 B1 | 2/2009 | Ciamacco, Jr. |
| 7,553,325 B2 | 6/2009 | Stinson |
| 7,578,838 B2 | 8/2009 | Melsheimer |
| 7,606,615 B2 | 10/2009 | Makower et al. |
| 7,625,400 B2 | 12/2009 | Bowe et al. |
| 7,625,401 B2 | 12/2009 | Clifford et al. |
| 7,641,647 B2 | 1/2010 | Gunderson |
| 7,655,040 B2 | 2/2010 | Douk et al. |
| 7,691,125 B2 | 4/2010 | Ducharme |
| 7,691,461 B1 | 4/2010 | Prabhu |
| 7,713,552 B2 | 5/2010 | Bleyer et al. |
| 7,758,520 B2 | 7/2010 | Griffin et al. |
| 7,771,462 B1 | 8/2010 | Davidson et al. |
| 7,771,463 B2 | 8/2010 | Ton et al. |
| 7,771,464 B2 | 8/2010 | Brightbill |
| 7,819,841 B2 | 10/2010 | Horrigan |
| 7,833,597 B2 | 11/2010 | Bavaro et al. |
| 7,879,024 B2 | 2/2011 | Thorstenson et al. |
| 7,892,274 B2 | 2/2011 | Will et al. |
| RE42,244 E | 3/2011 | Boatman et al. |
| 7,922,754 B2 | 4/2011 | Feld et al. |

(56) References Cited

U.S. PATENT DOCUMENTS

| | | |
|---|---|---|
| 7,930,014 B2 | 4/2011 | Huennekens et al. |
| 7,959,999 B2 | 6/2011 | Prabhu |
| 7,967,807 B2 | 6/2011 | Murray |
| 8,019,404 B2 | 9/2011 | Kapadia |
| 8,021,418 B2 | 9/2011 | Gerberding et al. |
| 8,048,139 B2 | 11/2011 | Frid et al. |
| 8,048,146 B2 | 11/2011 | Young et al. |
| 8,052,740 B2 | 11/2011 | Asano |
| 8,057,396 B2 | 11/2011 | Forster et al. |
| 8,057,529 B2 | 11/2011 | Cox et al. |
| 8,062,349 B2 | 11/2011 | Moore et al. |
| 8,075,606 B2 | 12/2011 | Dorn et al. |
| 8,092,509 B2 | 1/2012 | Dorn et al. |
| 8,114,144 B2 | 2/2012 | Chow et al. |
| 2002/0019659 A1 | 2/2002 | Goicoechea et al. |
| 2002/0072705 A1 | 6/2002 | Vrba et al. |
| 2002/0120323 A1 | 8/2002 | Thompson et al. |
| 2002/0165598 A1 | 11/2002 | Wahr et al. |
| 2002/0169377 A1 | 11/2002 | Khairkhahan et al. |
| 2002/0173835 A1 | 11/2002 | Bourang et al. |
| 2002/0193862 A1 | 12/2002 | Mitelberg et al. |
| 2002/0193872 A1 | 12/2002 | Trout et al. |
| 2002/0198559 A1 | 12/2002 | Mistry et al. |
| 2003/0050686 A1 | 3/2003 | Raeder-Devens et al. |
| 2003/0055482 A1 | 3/2003 | Schwager et al. |
| 2003/0083615 A1 | 5/2003 | Dance et al. |
| 2003/0097169 A1 | 5/2003 | Brucker et al. |
| 2003/0105426 A1 | 6/2003 | Jorgensen |
| 2003/0121148 A1 | 7/2003 | DiCaprio |
| 2003/0135256 A1 | 7/2003 | Gallagher et al. |
| 2003/0167052 A1 | 9/2003 | Lee et al. |
| 2003/0187495 A1 | 10/2003 | Cully et al. |
| 2003/0204236 A1 | 10/2003 | Letort |
| 2004/0006380 A1 | 1/2004 | Buck et al. |
| 2004/0015228 A1 | 1/2004 | Lombardi et al. |
| 2004/0015229 A1 | 1/2004 | Fulkerson et al. |
| 2004/0064042 A1 | 4/2004 | Nutting et al. |
| 2004/0068190 A1 | 4/2004 | Cespedes |
| 2004/0073283 A1 | 4/2004 | Ewers |
| 2004/0073287 A1 | 4/2004 | Goicoechea et al. |
| 2004/0073291 A1 | 4/2004 | Brown et al. |
| 2004/0088039 A1 | 5/2004 | Lee et al. |
| 2004/0093058 A1 | 5/2004 | Cottone et al. |
| 2004/0098086 A1 | 5/2004 | Goicoechea et al. |
| 2004/0111143 A1 | 6/2004 | Fischell et al. |
| 2004/0167599 A1 | 8/2004 | Goicoechea et al. |
| 2004/0167619 A1 | 8/2004 | Case et al. |
| 2004/0199240 A1 | 10/2004 | Dorn et al. |
| 2004/0215168 A1 | 10/2004 | Verrier et al. |
| 2004/0215314 A1 | 10/2004 | Kantor et al. |
| 2004/0254627 A1 | 12/2004 | Thompson et al. |
| 2004/0254637 A1 | 12/2004 | Yang et al. |
| 2004/0267280 A1 | 12/2004 | Nishide et al. |
| 2004/0267281 A1 | 12/2004 | Harari et al. |
| 2005/0004649 A1 | 1/2005 | Mistry et al. |
| 2005/0027306 A1 | 2/2005 | Krivoruchko et al. |
| 2005/0033403 A1 | 2/2005 | Ward et al. |
| 2005/0038493 A1 | 2/2005 | Feeser et al. |
| 2005/0038496 A1 | 2/2005 | Jones et al. |
| 2005/0049574 A1 | 3/2005 | Petrick et al. |
| 2005/0049666 A1 | 3/2005 | Chien et al. |
| 2005/0060025 A1 | 3/2005 | Mackiewicz et al. |
| 2005/0070794 A1 | 3/2005 | Deal et al. |
| 2005/0107865 A1 | 5/2005 | Clifford et al. |
| 2005/0154442 A1 | 7/2005 | Eidenschink et al. |
| 2005/0171591 A1 | 8/2005 | McHale et al. |
| 2005/0192498 A1 | 9/2005 | Miller et al. |
| 2005/0222673 A1 | 10/2005 | Nicholas |
| 2005/0228479 A1 | 10/2005 | Pavcnik et al. |
| 2005/0246008 A1 | 11/2005 | Hogendijk et al. |
| 2005/0246009 A1 | 11/2005 | Toner et al. |
| 2005/0255317 A1 | 11/2005 | Bavaro et al. |
| 2005/0273052 A1 | 12/2005 | Jorgensen |
| 2005/0278011 A1 | 12/2005 | Peckham |
| 2005/0283226 A1 | 12/2005 | Haverkost |
| 2006/0036309 A1 | 2/2006 | Hebert et al. |
| 2006/0064064 A1 | 3/2006 | Jang |
| 2006/0074477 A1* | 4/2006 | Berthiaume et al. ......... 623/1.11 |
| 2006/0079952 A1 | 4/2006 | Kaplan et al. |
| 2006/0116750 A1 | 6/2006 | Hebert et al. |
| 2006/0149355 A1 | 7/2006 | Mitelberg et al. |
| 2006/0184225 A1* | 8/2006 | Pryor ......................... 623/1.11 |
| 2006/0212105 A1 | 9/2006 | Dorn et al. |
| 2006/0241741 A1 | 10/2006 | Lootz |
| 2006/0259123 A1 | 11/2006 | Dorn et al. |
| 2006/0271154 A1 | 11/2006 | Woodall |
| 2006/0282149 A1 | 12/2006 | Kao |
| 2007/0027521 A1 | 2/2007 | Andreas et al. |
| 2007/0043419 A1 | 2/2007 | Nikolchev et al. |
| 2007/0073331 A1 | 3/2007 | Brown et al. |
| 2007/0083252 A1 | 4/2007 | McDonald |
| 2007/0100425 A1 | 5/2007 | Sequin et al. |
| 2007/0135818 A1 | 6/2007 | Moore et al. |
| 2007/0156230 A1 | 7/2007 | Dugan et al. |
| 2007/0168015 A1 | 7/2007 | Momma et al. |
| 2007/0173920 A1 | 7/2007 | Eidenschink |
| 2007/0185559 A1 | 8/2007 | Shelso |
| 2007/0191708 A1 | 8/2007 | Gerold et al. |
| 2007/0191924 A1 | 8/2007 | Rudakov |
| 2007/0208301 A1 | 9/2007 | Evard et al. |
| 2007/0225788 A1 | 9/2007 | Fischell et al. |
| 2007/0225790 A1 | 9/2007 | Fischell et al. |
| 2007/0255386 A1 | 11/2007 | Tenne |
| 2007/0266542 A1 | 11/2007 | Melsheimer |
| 2007/0270691 A1 | 11/2007 | Bailey et al. |
| 2007/0287957 A1 | 12/2007 | Magnuson et al. |
| 2007/0288082 A1 | 12/2007 | Williams |
| 2007/0299498 A1 | 12/2007 | Perez et al. |
| 2007/0299500 A1 | 12/2007 | Hebert et al. |
| 2007/0299501 A1 | 12/2007 | Hebert et al. |
| 2007/0299502 A1 | 12/2007 | Hebert et al. |
| 2008/0004689 A1 | 1/2008 | Jahnke et al. |
| 2008/0004690 A1 | 1/2008 | Robaina |
| 2008/0009932 A1 | 1/2008 | Ta et al. |
| 2008/0009933 A1 | 1/2008 | Ta et al. |
| 2008/0015499 A1 | 1/2008 | Warnack |
| 2008/0015610 A1 | 1/2008 | Kaplan et al. |
| 2008/0021535 A1 | 1/2008 | Leopold et al. |
| 2008/0027378 A1 | 1/2008 | Hayman et al. |
| 2008/0027528 A1 | 1/2008 | Jagger et al. |
| 2008/0033525 A1 | 2/2008 | Shaked et al. |
| 2008/0033533 A1 | 2/2008 | Borck et al. |
| 2008/0045773 A1 | 2/2008 | Popowski et al. |
| 2008/0046064 A1 | 2/2008 | Sequin et al. |
| 2008/0046072 A1 | 2/2008 | Laborde et al. |
| 2008/0051867 A1 | 2/2008 | Davila et al. |
| 2008/0051870 A1* | 2/2008 | Kaufmann ................ 623/1.11 |
| 2008/0077223 A1 | 3/2008 | Fischell et al. |
| 2008/0082155 A1 | 4/2008 | Fischell et al. |
| 2008/0097404 A1 | 4/2008 | Yribarren et al. |
| 2008/0108902 A1 | 5/2008 | Nita et al. |
| 2008/0108987 A1 | 5/2008 | Bruszewski et al. |
| 2008/0125852 A1 | 5/2008 | Garrison et al. |
| 2008/0147160 A1 | 6/2008 | Ghione et al. |
| 2008/0188803 A1 | 8/2008 | Jang |
| 2008/0195137 A1 | 8/2008 | Alleyne et al. |
| 2008/0208307 A1 | 8/2008 | Ben-Muvhar et al. |
| 2008/0208311 A1 | 8/2008 | Kao et al. |
| 2008/0208319 A1 | 8/2008 | Rabkin et al. |
| 2008/0215129 A1 | 9/2008 | Venturelli et al. |
| 2008/0228260 A1 | 9/2008 | Hannay |
| 2008/0234795 A1 | 9/2008 | Snow et al. |
| 2008/0234796 A1 | 9/2008 | Dorn |
| 2008/0243069 A1 | 10/2008 | Krivoruchko |
| 2008/0243222 A1 | 10/2008 | Schafersman et al. |
| 2008/0255447 A1 | 10/2008 | Bourang et al. |
| 2008/0255506 A1 | 10/2008 | Wilson |
| 2008/0255654 A1 | 10/2008 | Hebert et al. |
| 2008/0269675 A1 | 10/2008 | Balgobin et al. |
| 2008/0288056 A1 | 11/2008 | Simpson et al. |
| 2009/0005858 A1 | 1/2009 | Young et al. |
| 2009/0024205 A1 | 1/2009 | Hebert et al. |
| 2009/0048654 A1 | 2/2009 | Chmura et al. |
| 2009/0048655 A1 | 2/2009 | Jang |

(56) References Cited

U.S. PATENT DOCUMENTS

| | | |
|---|---|---|
| 2009/0062899 A1 | 3/2009 | Dang et al. |
| 2009/0069882 A1 | 3/2009 | Venturelli et al. |
| 2009/0082840 A1 | 3/2009 | Rusk et al. |
| 2009/0124899 A1 | 5/2009 | Jacobs et al. |
| 2009/0131785 A1 | 5/2009 | Lee et al. |
| 2009/0132024 A1 | 5/2009 | Berkhoff |
| 2009/0138065 A1 | 5/2009 | Zhang et al. |
| 2009/0182409 A1 | 7/2009 | Feld et al. |
| 2009/0198317 A1 | 8/2009 | Ciamacco, Jr. |
| 2009/0204203 A1 | 8/2009 | Allen et al. |
| 2009/0209856 A1 | 8/2009 | Tanaka et al. |
| 2009/0209910 A1 | 8/2009 | Kugler et al. |

OTHER PUBLICATIONS

International Search Report and Written Opinion mailed Oct. 7, 2013.

\* cited by examiner

ENDOVASCULAR DELIVERY SYSTEM WITH AN IMPROVED RADIOPAQUE MARKER SCHEME

CROSS-REFERENCE TO RELATED APPLICATIONS

This application claims the benefit of U.S. Provisional Application No. 61/660,413, filed Jun. 15, 2012, the contents of which are incorporated by reference herein.

FIELD OF THE INVENTION

The present invention is related to an endovascular delivery system for an endovascular prosthesis. More particularly, the present invention is related to an endovascular delivery system including an improved radiopaque marker system for accurate delivery of the prosthesis.

BACKGROUND OF THE INVENTION

An aneurysm is a medical condition indicated generally by an expansion and weakening of the wall of an artery of a patient. Aneurysms can develop at various sites within a patient's body. Thoracic aortic aneurysms (TAAs) or abdominal aortic aneurysms (AAAs) are manifested by an expansion and weakening of the aorta which is a serious and life threatening condition for which intervention is generally indicated. Existing methods of treating aneurysms include invasive surgical procedures with graft replacement of the affected vessel or body lumen or reinforcement of the vessel with a graft.

Surgical procedures to treat aortic aneurysms can have relatively high morbidity and mortality rates due to the risk factors inherent to surgical repair of this disease as well as long hospital stays and painful recoveries. This is especially true for surgical repair of TAAs, which is generally regarded as involving higher risk and more difficulty when compared to surgical repair of AAAs. An example of a surgical procedure involving repair of a AAA is described in a book titled Surgical Treatment of Aortic Aneurysms by Denton A. Cooley, M. D., published in 1986 by W.B. Saunders Company.

Due to the inherent risks and complexities of surgical repair of aortic aneurysms, endovascular repair has become a widely-used alternative therapy, most notably in treating AAAs. Early work in this field is exemplified by Lawrence, Jr. et al. in "Percutaneous Endovascular Graft Experimental Evaluation", Radiology (May 1987) and by Mirich et al. in "Percutaneously Placed Endovascular Grafts for Aortic Aneurysms: Feasibility Study," Radiology (March 1989). Commercially available endoprostheses for the endovascular treatment of AAAs include the AneuRx® stent graft manufactured by Medtronic, Inc. of Minneapolis, Minn., the Zenith® stent graft system sold by Cook, Inc. of Bloomington, Ind., the PowerLink® stent-graft system manufactured by Endologix, Inc. of Irvine, Calif., and the Excluder® stent graft system manufactured by W.L. Gore & Associates, Inc. of Newark, Del. A commercially available stent graft for the treatment of TAAs is the TAG™ system manufactured by W.L. Gore & Associates, Inc.

When deploying devices by catheter or other suitable instrument, it is advantageous to have a flexible and low profile stent graft and delivery system for passage through the various guiding catheters as well as the patient's sometimes tortuous anatomy. Many of the existing endovascular devices and methods for treatment of aneurysms, while representing significant advancement over previous devices and methods, use systems having relatively large transverse profiles, often up to 24 French. Also, such existing systems have greater than desired lateral stiffness, which can complicate the delivery process. In addition, the sizing of stent grafts may be important to achieve a favorable clinical result. In order to properly size a stent graft, the treating facility typically must maintain a large and expensive inventory of stent grafts in order to accommodate the varied sizes of patient vessels due to varied patient sizes and vessel morphologies. Alternatively, intervention may be delayed while awaiting custom size stent grafts to be manufactured and sent to the treating facility. As such, minimally invasive endovascular treatment of aneurysms is not available for many patients that would benefit from such a procedure and can be more difficult to carry out for those patients for whom the procedure is indicated. What have been needed are stent graft systems, delivery systems and methods that are adaptable to a wide range of patient anatomies and that can be safely and reliably deployed using a flexible low profile system.

SUMMARY OF THE INVENTION

In one embodiment, the present invention is directed to an endovascular delivery system that includes an elongate outer tubular device having an open lumen and opposed proximal and distal ends with a medial portion therein between. Within the outer tubular device, there is a prosthesis holder that may include an axial guidewire extending through the middle of the prosthesis holder and a body surrounding the axial guidewire, the body including at least two generally cylindrical markers aligned in a direction parallel to the axial guidewire and each spaced an equal distance from the axial guidewire. The prosthesis holder also includes an outer surface, upon which a prosthesis may be secured prior to delivery.

The present invention also provides a method of delivering a prosthesis within a body lumen, which such method includes the step of providing a delivery system. The delivery system includes an elongate outer tubular device having an open lumen and opposed proximal and distal ends with a medial portion therein between. The system may also include a prosthesis holder disposed within the outer tubular device. The prosthesis holder may include an axial guidewire extending through the prosthesis holder and a body surrounding the axial guidewire, the body having at least two generally cylindrical markers aligned in a direction parallel to the axial guidewire and each spaced an equal distance from the axial guidewire. The holder may also include an outer surface and a prosthesis secured to the outer surface. The method then includes the step of inserting the delivery system within a body lumen and directing the prosthesis holder to a desired location within the lumen. The method includes the step of using a known device that provides imaging, such as a radiographic or fluoroscopy monitor, to view the location of the generally cylindrical markers. The method includes the step of aligning the prosthesis holder at a rotational angle based upon the generally cylindrical markers and releasing the prosthesis within the body lumen.

In some aspects of the present invention, the endovascular prosthesis may be a modular endovascular graft assembly including a bifurcated main graft member formed from a supple graft material having a main fluid flow lumen therein. The main graft member may also include an ipsilateral leg with an ipsilateral fluid flow lumen in communication with the main fluid flow lumen, a contralateral leg with a contralateral fluid flow lumen in communication with the main fluid flow lumen and a network of inflatable channels disposed on the main graft member. The network of inflatable channels may be disposed anywhere on the main graft member including the ipsilateral and contralateral legs. The network of inflatable channels may be configured to accept a hardenable fill or inflation material to provide structural rigidity to the main graft member when the network of inflatable channels is in an inflated state. The network of inflatable channels may also include at least one inflatable cuff disposed on a proximal portion of the main graft member which is configured to seal against an inside surface of a patient's vessel. The fill material can also have transient or chronic radiopacity to facilitate the placement of the modular limbs into the main graft member. A proximal anchor member may be disposed at a proximal end of the main graft member and be secured to the main graft member. The proximal anchor member may have a self-expanding proximal stent portion secured to a self-expanding distal stent portion with struts having a cross sectional area that is substantially the same as or greater than a cross sectional area of proximal stent portions or distal stent portions adjacent the strut. At least one ipsilateral graft extension having a fluid flow lumen disposed therein may be deployed with the fluid flow lumen of the graft extension sealed to and in fluid communication with the fluid flow lumen of the ipsilateral leg of the main graft member. At least one contralateral graft extension having a fluid flow lumen disposed therein may be deployed with the fluid flow lumen of the graft extension sealed to and in fluid communication with the fluid flow lumen of the contralateral leg of the main graft member. For some embodiments, an outside surface of the graft extension may be sealed to an inside surface of the contralateral leg of the main graft when the graft extension is in a deployed state. For some embodiments, the axial length of the ipsilateral and contralateral legs may be sufficient to provide adequate surface area contact with outer surfaces of graft extensions to provide sufficient friction to hold the graft extensions in place. For some embodiments, the ipsilateral and contralateral legs may have an axial length of at least about 2 cm. For some embodiments, the ipsilateral and contralateral legs may have an axial length of about 2 cm to about 6 cm, more specifically, about 3 cm to about 5 cm.

These and other features and advantages of the present invention will become apparent from the following detailed description of illustrative embodiments thereof, which is to be read in connection with the accompanying drawings. Corresponding reference element numbers or characters indicate corresponding parts throughout the several views of the drawings.

DETAILED DESCRIPTION OF THE INVENTION

Embodiments of the invention are directed generally to methods and devices for treatment of fluid flow vessels with the body of a patient. Treatment of blood vessels is specifically indicated for some embodiments, and, more specifically, treatment of aneurysms, such as abdominal aortic aneurysms. With regard to graft embodiments discussed herein and components thereof, the term "proximal" refers to a location towards a patient's heart and the term "distal" refers to a location away from the patient's heart. With regard to delivery system catheters and components thereof discussed herein, the term "distal" refers to a location that is disposed away from an operator who is using the catheter and the term "proximal" refers to a location towards the operator.

Figure 1:
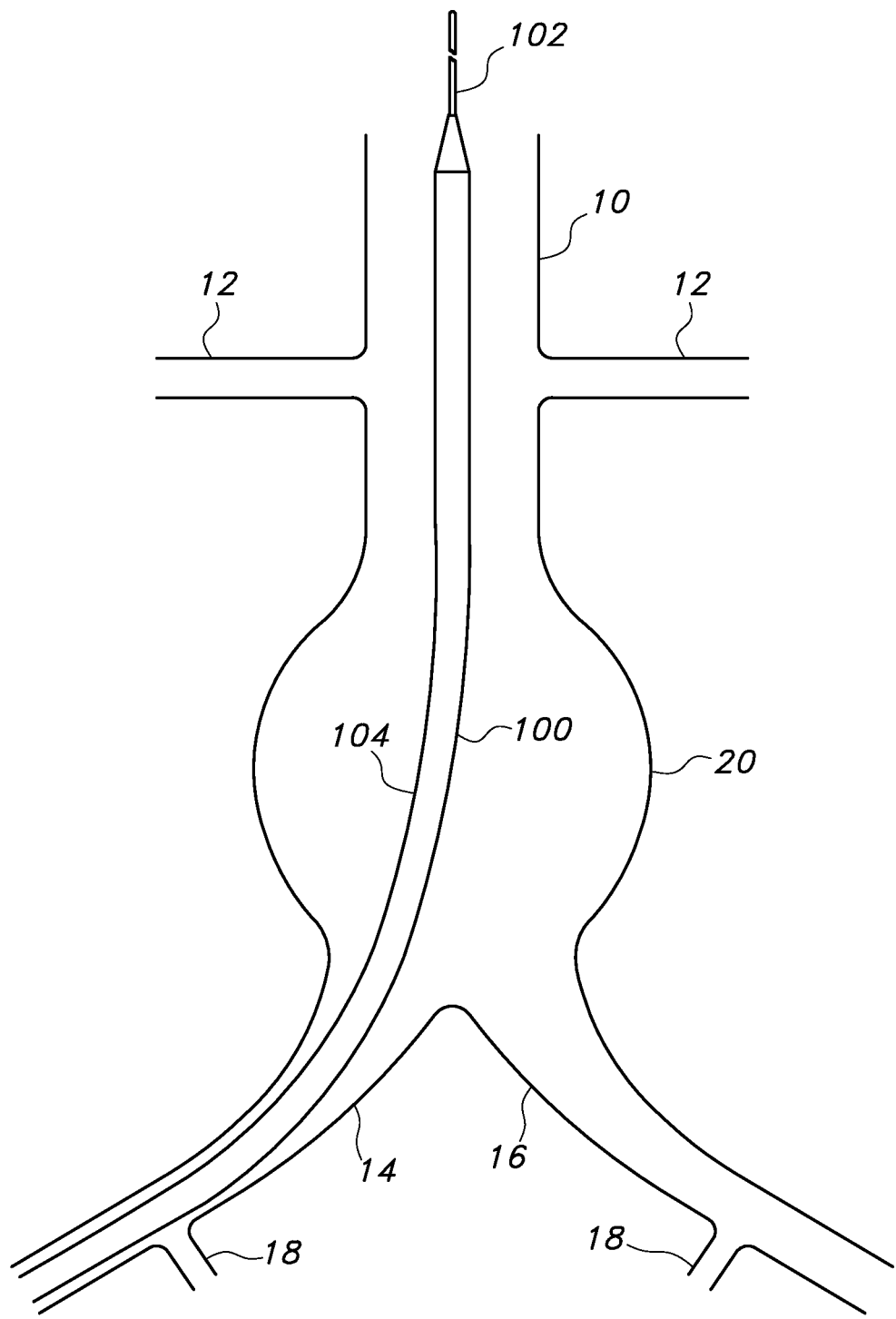
FIG. 1 depicts an initial deployment state of the endovascular delivery system of the present invention within a patient's vasculature.

FIG. 1 illustrates an embodiment of a deployment sequence of an embodiment of a endovascular prosthesis (not shown), such as a modular graft assembly. For endovascular methods, access to a patient's vasculature may be achieved by performing an arteriotomy or cut down to the patient's femoral artery or by other common techniques, such as the percutaneous Seldinger technique. For such techniques, a delivery sheath (not shown) may be placed in communication with the interior of the patient's vessel such as the femoral artery with the use of a dilator and guidewire assembly. Once the delivery sheath is positioned, access to the patient's vasculature may be achieved through the delivery sheath which may optionally be sealed by a hemostasis valve or other suitable mechanism. For some procedures, it may be necessary to obtain access via a delivery sheath or other suitable means to both femoral arteries of a patient with the delivery sheaths directed upstream towards the patient's aorta. In some applications a delivery sheath may not be needed and the delivery catheter of the present invention may be directly inserted into the patient's access vessel by either arteriotomy or percutaneous puncture. Once the delivery sheath or sheaths have been properly positioned, an endovascular delivery catheter or system, typically containing an endovascular prosthesis such as but not limited to an inflatable stent-graft, may then be advanced over a guidewire through the delivery sheath and into the patient's vasculature.

FIG. 1 depicts the initial placement of the endovascular delivery system 100 of the present invention within a patient's vasculature. The endovascular delivery system 100 may be advanced along a guidewire 102 proximally upstream of blood flow into the vasculature of the patient including iliac arteries 14, 16 and aorta 10 shown in FIG. 1. While the iliac arties 14, 16 may be medically described as the right and left common iliac arteries, respectively, as used herein iliac artery 14 is described as an ipsilateral iliac artery and iliac artery 16 is described as a contralateral iliac artery. The flow of the patient's blood (not shown) is in a general downward direction in FIG. 1. Other vessels of the patient's vasculature shown in FIG. 1 include the renal arteries 12 and hypogastric arteries 18.

The endovascular delivery system 100 may be advanced into the aorta 10 of the patient until the endovascular prosthesis (not shown) is disposed substantially adjacent an aortic aneurysm 20 or other vascular defect to be treated. The portion of the endovascular delivery system 100 that is advance through bodily lumens is desirably a low profile delivery system, for example having an overall outer diameter of less than 14 French. Other French sizes are also useful, such as but not limited to less than 12 French, less than 10 French, or any sized from 10 to 14 French. Once the endovascular delivery system 100 is so positioned, an outer sheath 104 of the endovascular delivery system 100 may be retracted distally so as to expose the prosthesis (not shown) which has been compressed and compacted to fit within the inner lumen of the outer sheath 104 of the endovascular delivery system 100.

Figure 2:
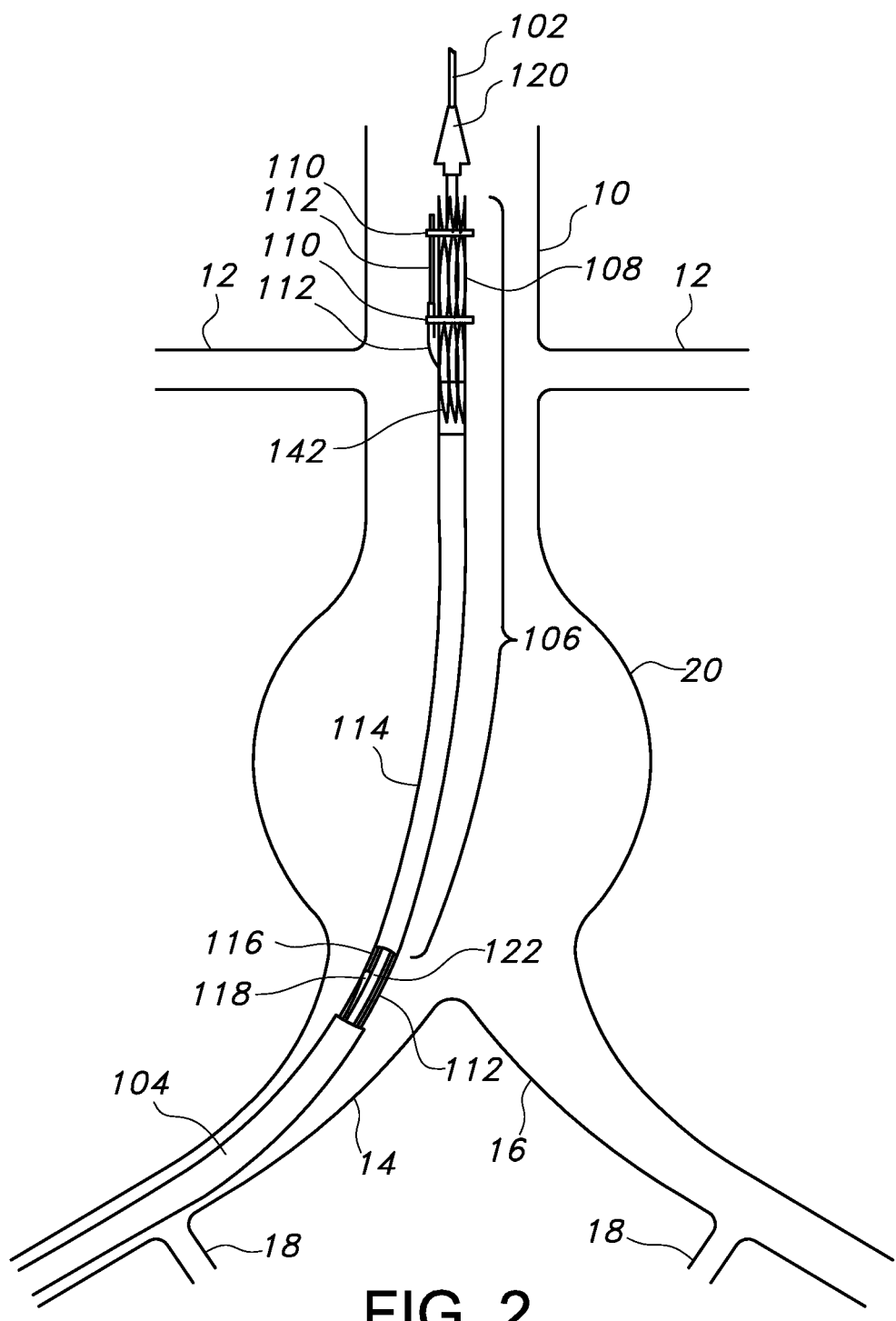
FIG. 2 depicts a deployment state of the endovascular delivery system of the present invention within a patient's vasculature after withdrawal of an outer sheath.

As depicted in FIG. 2, once the endovascular delivery system 100 is so positioned, the outer sheath 104 of the endovascular delivery system 100 may be retracted distally so as to expose the endovascular prosthesis 106 which has been compressed and compacted to fit within the inner lumen of the outer sheath 104 of the endovascular delivery system 100. The outer sheath 104 may be formed of a body compatible material. Desirably, the biocompatible material may be a biocompatible polymer. Examples of suitable biocompatible polymers may include, but are not limited to, polyolefins such as polyethylene (PE), high density polyethylene (HDPE) and polypropylene (PP), polyolefin copolymers and terpolymers, polytetrafluoroethylene (PTFE), polyethylene terephthalate (PET), polyesters, polyamides, polyurethanes, polyurethaneureas, polypropylene and, polycarbonates, polyvinyl acetate, thermoplastic elastomers including polyether-polyester block copolymers and polyamide/polyether/polyesters elastomers, polyvinyl chloride, polystyrene, polyacrylate, polymethacrylate, polyacrylonitrile, polyacrylamide, silicone resins, combinations and copolymers thereof, and the like. Desirably, the biocompatible polymers include polypropylene (PP), polytetrafluoroethylene (PTFE), polyethylene terephthalate (PET), high density polyethylene (HDPE), combinations and copolymers thereof, and the like. Useful coating materials may include any suitable biocompatible coating. Non-limiting examples of suitable coatings include polytetrafluoroethylene, silicone, hydrophilic materials, hydrogels, and the like. Useful hydrophilic coating materials may include, but are not limited to, alkylene glycols, alkoxy polyalkylene glycols such as methoxypolyethylene oxide, polyoxyalkylene glycols such as polyethylene oxide, polyethylene oxide/polypropylene oxide copolymers, polyalkylene oxide-modified polydimethylsiloxanes, polyphosphazenes, poly(2-ethyl-2-oxazoline), homopolymers and copolymers of (meth)acrylic acid, poly(acrylic acid), copolymers of maleic anhydride including copolymers of methylvinyl ether and maleic acid, pyrrolidones including poly(vinylpyrrolidone)homopolymers and copolymers of vinyl pyrrolidone, poly(vinylsulfonic acid), acryl amides including poly(N-alkylacrylarnide), poly(vinyl alcohol), poly(ethyleneimine), polyamides, poly(carboxylic acids), methyl cellulose, carboxymethylcellulose, hydroxypropyl cellulose, polyvinylsulfonic acid, water soluble nylons, heparin, dextran, modified dextran, hydroxylated chitin, chondroitin sulphate, lecithin, hyaluranon, combinations and copolymers thereof, and the like. Non-limiting examples of suitable hydrogel coatings include polyethylene oxide and its copolymers, polyvinylpyrrolidone and its derivatives; hydroxyethylacrylates or hydroxyethyl(meth)acrylates; polyacrylic acids; polyacrylamides; polyethylene maleic anhydride, combinations and copolymers thereof, and the like. Desirably, the outer sheath 104 may be made of polymeric materials, e.g., polyimides, polyester elastomers (Hytrel®), or polyether block amides (Pebax®), polytetrafluoroethylene, and other thermoplastics and polymers. The outside diameter of the outer sheath 104 may range from about 0.1 inch to about 0.4 inch. The wall thickness of the outer sheath 104 may range from about 0.002 inch to about 0.015 inch. The outer sheath 104 may also include an outer hydrophilic coating. Further, the outer sheath 104 may include an internal braided portion of either metallic or polymeric filaments. In addition to being radially compressed when disposed within an inner lumen of the outer sheath 104 of the endovascular delivery system 100, a proximal stent 108 may be radially restrained by high strength flexible belts 110 in order to maintain a small profile and avoid engagement of the proximal stent 108 with a body lumen wall until deployment of the proximal stent 108 is initiated. The belts 110 can be made from any high strength, resilient material that can accommodate the tensile requirements of the belt members and remain flexible after being set in a constraining configuration. Typically, belts 110 are made from solid ribbon or wire of a shape memory alloy such as nickel titanium or the like, although other metallic or polymeric materials are possible. Belts 110 may also be made of braided metal filaments or braided or solid filaments of high strength synthetic fibers such as Dacron®, Spectra or the like. An outside transverse cross section of the belts 110 may range from about 0.002 to about 0.012 inch, specifically, about 0.004 to about 0.007 inch. The cross sections of belts 21, 22 and 23 may generally take on any shape, including rectangular (in the case of a ribbon), circular, elliptical, square, etc. The ends of the belts 110 may be secured by one or more stent release wires or elongate rods 112 which extend through looped ends (not shown) of the belts 110. The stent release wires or elongate rods 112 may be disposed generally within the prosthesis 106 during delivery of the system 100 to the desired bodily location. For example, the stent release wires or elongate rods 112 may enter and exit the guidewire lumen 122 or other delivery system lumen as desired to affect controlled release of the stent 108, including if desired controlled and staged release of the stent 108. Once the outer sheath 104 of the endovascular delivery system 100 has been retracted, the endovascular delivery system 100 and the endovascular prosthesis 106 may be carefully positioned in an axial direction such that the proximal stent 108 is disposed substantially even with the renal arteries.

Desirably, the endovascular prosthesis 106 includes an inflatable graft 114. The inflatable graft may be a bifurcated graft having a main graft body 124, an ipsilateral graft leg and a contralateral graft leg 128. The inflatable graft 114 may further include a fill port 116 in fluid communication with an inflation tube of the endovascular delivery system 100 for providing an inflation medium (not shown). The distal portion of the endovascular delivery system 100 may include a nosecone 120 which provides an atraumatic distal portion of the endovascular delivery system 100. The guidewire 102 is slidably disposed within a guidewire lumen 122 of the endovascular delivery system 100.

Figure 3:
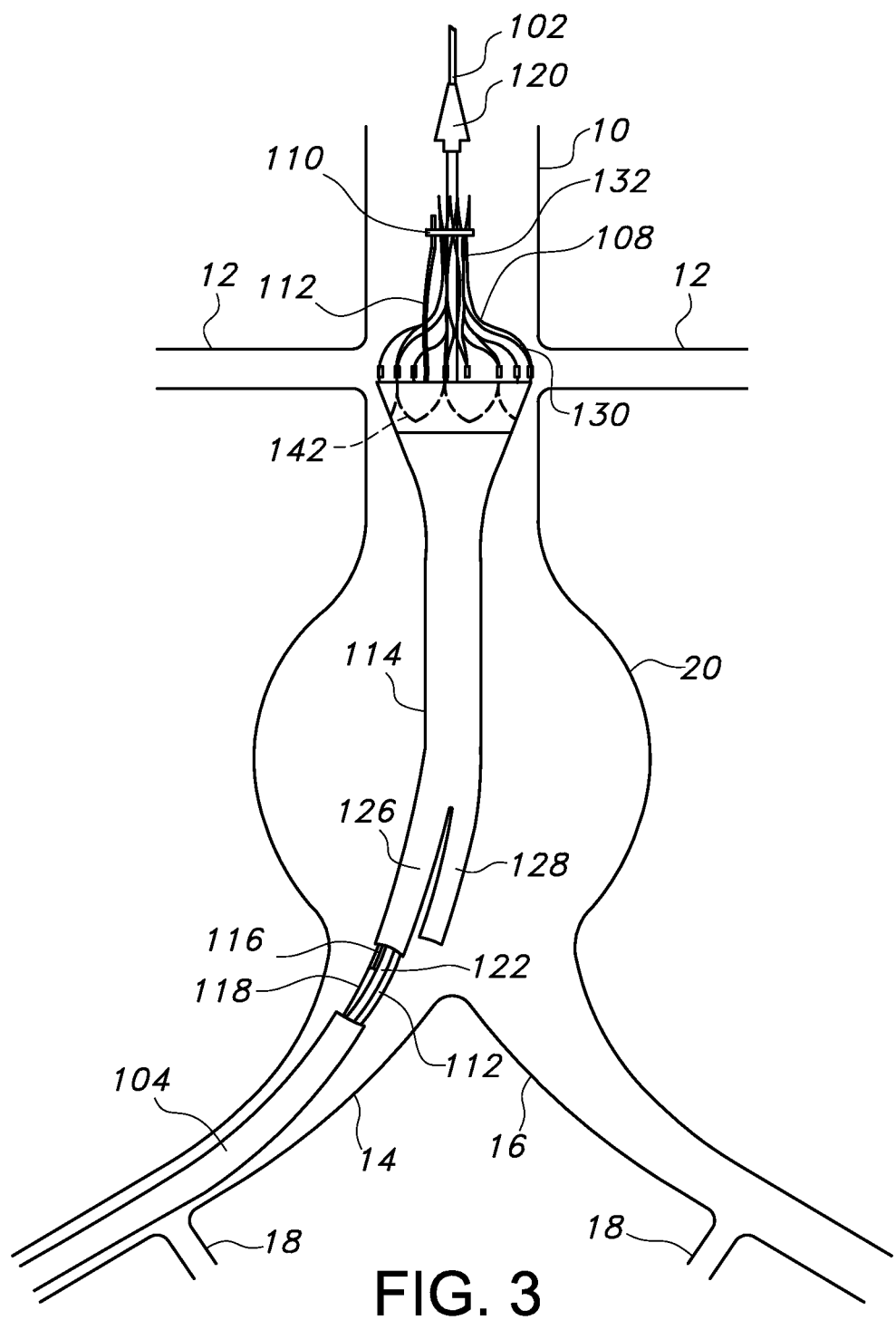
FIG. 3 depicts a deployment state of the endovascular delivery system of the present invention within a patient's vasculature after an initial and partial stent deployment.

As depicted in FIG. 3, deployment of the proximal stent 108 may begin with deployment of the distal portion 130 of stent 108 by retracting the stent release wire or rod 112 that couples ends of belt 110 restraining the distal portion 130 of the stent 108. The distal portion 130 of stent 108 may be disposed to the main graft body 124 via a connector ring 142. The stent 108 and/or the connector ring 142 may be made from or include any biocompatible material, including metallic materials, such as but not limited to, nitinol, cobalt-based alloy such as Elgiloy, platinum, gold, stainless steel, titanium, tantalum, niobium, and combinations thereof. The present invention, however, is not limited to the use of such a connector ring 142 and other shaped connectors for securing the distal portion 130 of the stent 108 at or near the end of the main graft body 124 may suitably be used. Additional axial positioning may typically be carried out even after deploying the distal portion 130 of the stent 108. This may still be carried out in many circumstances as the proximal portion 132 of the stent 108 does not include tissue engaging barbs (not shown) for some embodiments and will provide only partial outward radial contact or frictional force on the inner lumen of the patient's vessel or aorta 10 until the proximal portion 132 of the stent 108 is deployed. Once the belt 110 constraining the proximal portion 132 of the stent 108 has been released, the proximal portion 132 of the stent 108 self-expands in an outward radial direction until an outside surface of the proximal portion 132 of the stent 108 makes contact with and engages an inner surface of the patient's vessel 10.

Figure 4:
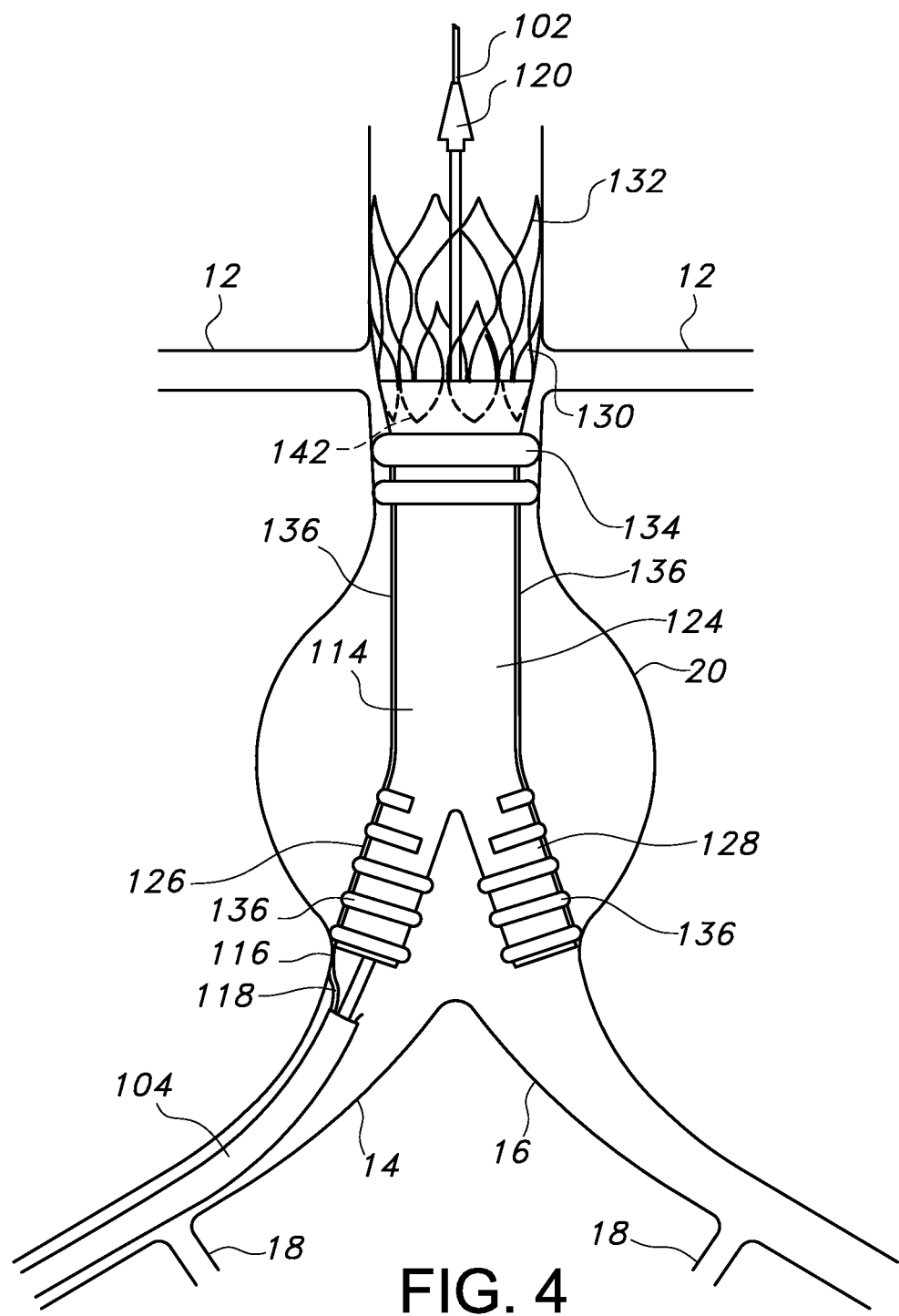
FIG. 4 depicts a deployment state of the endovascular delivery system of the present invention within a patient's vasculature after a stent deployment.

As depicted in FIG. 4, after the distal portion 130 of the stent 108 has been deployed, the proximal portion 132 of the stent 108 may then be deployed by retracting the wire 112 that couples the ends of the belt 110 restraining the proximal portion 132 of the stent 108. As the proximal portion 132 of the stent 108 self-expands in an outward radial direction, an outside surface of the proximal portion 132 of the stent 108 eventually makes contact with the inside surface of the patient's aorta 10. For embodiments that include tissue engaging barbs (not shown) on the proximal portion 132 of the stent 108, the barbs may also be oriented and pushed in an outward radial direction so as to make contact and engage the inner surface tissue of the patient's vessel 10, which further secures the proximal stent 108 to the patient's vessel 10.

Once the proximal stent 108 has been secured to the inside surface of the patient's vessel 10, the proximal inflatable cuff 134 may then be filled through the inflation port 116 with inflation material injected through an inflation tube 118 of the endovascular delivery system 100 which may serve to seal an outside surface of the inflatable cuff 134 to the inside surface of the vessel 10. The remaining network of inflatable channels 136 are also filled with pressurized inflation material at the same time which provides a more rigid frame like structure to the inflatable graft 114. For some embodiments, the inflation material may be a curable or hardenable material that may cured or hardened once the network of inflatable channels 136 are filled to a desired level of material or pressure within the network. Some embodiments may also employ radiopaque inflation material to facilitate monitoring of the fill process and subsequent engagement of graft extensions (not shown). The material may be cured by any of the suitable methods discussed herein including time lapse, heat application, application of electromagnetic energy, ultrasonic energy application, chemical adding or mixing or the like. Some embodiments for the inflation material that may be used to provide outward pressure or a rigid structure from within the inflatable cuff 134 or network of inflatable channels 136 may include inflation materials formed from glycidyl ether and amine materials. Some inflation material embodiments may include an in situ formed hydrogel polymer having a first amount of diamine and a second amount of polyglycidyl ether wherein each of the amounts are present in a mammal or in a medical device, such as an inflatable graft, located in a mammal in an amount to produce an in situ formed hydrogel polymer that is biocompatible and has a cure time after mixing of about 10 seconds to about 30 minutes and wherein the volume of said hydrogel polymer swells less than 30 percent after curing and hydration. Some embodiments of the inflation material may include radiopaque material such as sodium iodide, potassium iodide, barium sulfate, Visipaque 320, Hypaque, Omnipaque 350, Hexabrix and the like. For some inflation material embodiments, the polyglycidyl ether may be selected from trimethylolpropane triglycidyl ether, sorbitol polyglycidyl ether, polyglycerol polyglycidyl ether, pentaerythritol polyglycidyl ether, diglycerol polyglycidyl ether, glycerol polyglycidyl ether, trimethylolpropane polyglycidyl ether, polyethylene glycol diglycidyl ether, resorcinol diglycidyl ether, glycidyl ester ether of p-hydroxy benzoic acid, neopentyl glycol diglycidyl ether, 1,6-hexanediol diglycidyl ether, bisphenol A $(PO)_2$ diglycidyl ether, hydroquinone diglycidyl ether, bisphenol S diglycidyl ether, terephthalic acid diglycidyl ester, and mixtures thereof. For some inflation material embodiments, the diamine may be selected from (poly)alkylene glycol having amino or alkylamino termini selected from the group consisting of polyethylene glycol (400) diamine, di-(3-aminopropyl) diethylene glycol r, polyoxypropylenediamine, polyetherdiamine, polyoxyethylenediamine, triethyleneglycol diamine and mixtures thereof. For some embodiments, the diamine may be hydrophilic and the polyglycidyl ether may be hydrophilic prior to curing. For some embodiments, the diamine may be hydrophilic and the polyglycidyl ether is hydrophobic prior to curing. For some embodiments, the diamine may be hydrophobic and the polyglycidyl ether may be hydrophilic prior to curing.

The network of inflatable channels 136 may be partially or fully inflated by injection of a suitable inflation material into the main fill port 116 to provide rigidity to the network of inflatable channels 136 and the graft 114. In addition, a seal is produced between the inflatable cuff 134 and the inside surface of the abdominal aorta 10. Although it is desirable to partially or fully inflate the network of inflatable channels 136 of the graft 114 at this stage of the deployment process, such inflation step optionally may be accomplished at a later stage if necessary.

Figure 5:
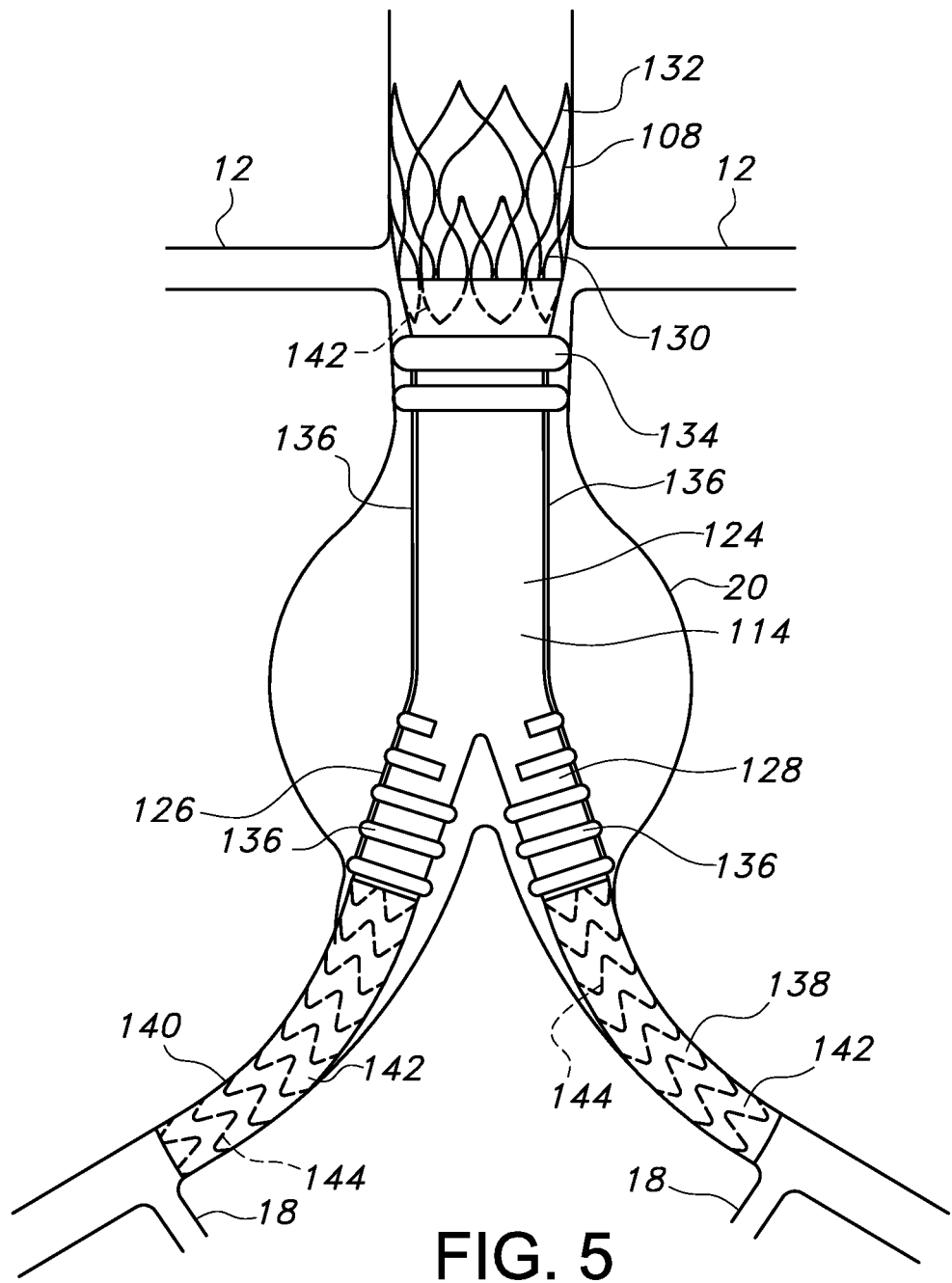
FIG. 5 depicts a deployed bifurcated endovascular prosthesis with graft leg extensions.

Once the graft 114 is anchored and the inflatable channels 136 thereof have been filled and expanded, another delivery catheter (not shown) may be used to deploy a contralateral graft extension 138, as depicted in FIG. 5. The contralateral graft extension 138 is in an axial position which overlaps the contralateral leg 128 of the graft 114. The amount of desired overlap of the graft extension 138 with the contralateral leg 128 may vary depending on a variety of factors including vessel morphology, degree of vascular disease, patient status and the like. However, for some embodiments, the amount of axial overlap between the contralateral graft extension 138 and the contralateral leg 128 may be about 1 cm to about 5 cm, more specifically, about 2 cm to about 4 cm. Once the contralateral graft extension 138 has been deployed, an ipsilateral graft extension may be similarly deployed in the ipsilateral graft leg 126.

For some deployment embodiments, the patient's hypogastric arteries may be used to serve as a positioning reference point to ensure that the hypogastric arteries are not blocked by the deployment. Upon such a deployment, the distal end of a graft extension 138 or 140 may be deployed anywhere within a length of the ipsilateral leg 126 or contralateral leg 128 of the graft 114. Also, although only one graft extension 140, 138 is shown deployed on the ipsilateral side and contralateral side of the graft assembly 114, additional graft extensions 140, 138 may be deployed within the already deployed graft extensions 140, 138 in order to achieve a desired length extension of the ipsilateral leg 126 or contralateral leg 128. For some embodiments, about 1 to about 5 graft extensions 138, 140 may be deployed on either the ipsilateral or contralateral sides of the graft assembly 114. Successive graft extensions 138, 140 may be deployed within each other so as to longitudinally overlap fluid flow lumens of successive graft extensions.

Graft extensions 138, 140, which may be interchangeable for some embodiments, or any other suitable extension devices or portions of the main graft section 124 may include a variety of suitable configurations. For some embodiments, graft extensions 138, 140 may include a polytetrafluoroethylene (PTFE) graft 142 with helical nitinol stent 144.

Further details of the endovascular prosthesis 106 and/or graft extensions 138, 140 may be found in commonly owned U.S. Pat. Nos. 6,395,019; 7,081,129; 7,147,660; 7,147,661; 7,150,758; 7,651,071; 7,766,954 and 8,167,927 and commonly owned U.S. Published Application No. 2009/0099649, the contents of all of which are incorporated herein by reference in their entirety. Details for the manufacture of the endovascular prosthesis 106 may be found in commonly owned U.S. Pat. Nos. 6,776,604; 7,090,693; 7,125,646; 7,147,455; 7,678,217 and 7,682,475, the contents of all of which are incorporated herein by reference in their entirety. Useful inflation materials for the inflatable graft 114 may be found in may be found in commonly owned U.S. Published Application No. 2005/0158272 and 2006/0222596, the contents of all of which are incorporated herein by reference in their entirety. Additional details of an endovascular delivery system having a bifurcated and inflatable prosthesis having a tether from a contralateral leg to restrain movement of the contralateral leg with respect to an ipsilateral leg of the prosthesis may be found in commonly owned U.S. Provisional Application No. 61/660,105, entitled "Bifurcated Endovascular Prosthesis Having Tethered Contralateral Leg", filed on Jun. 15, 2012, the contents of which are incorporated the herein by reference in their entirety. Additional details of an endovascular delivery system including an improved hypotube may be found in commonly owned U.S. Provisional Application No. 61/660, 103, entitled "Endovascular Delivery System With Flexible And Torqueable Hypotube", filed on Jun. 15, 2012, the contents of which are incorporated the herein by reference in their entirety.

Useful graft materials for the endovascular prosthesis 106 include, but are not limited, polyethylene; polypropylene; polyvinyl chloride; polytetrafluoroethylene (PTFE); fluorinated ethylene propylene; fluorinated ethylene propylene; polyvinyl acetate; polystyrene; poly(ethylene terephthalate); naphthalene dicarboxylate derivatives, such as polyethylene naphthalate, polybutylene naphthalate, polytrimethylene naphthalate and trimethylenediol naphthalate; polyurethane, polyurea; silicone rubbers; polyamides; polyimides; polycarbonates; polyaldehydes; polyether ether ketone; natural rubbers; polyester copolymers; silicone; styrene-butadiene copolymers; polyethers; such as fully or partially halogenated polyethers; and copolymers and combinations thereof. Desirably, the graft materials are non-textile graft materials, e.g., materials that are not woven, knitted, filament-spun, etc. that may be used with textile grafts. Such useful graft material may be extruded materials. Particularly useful materials include porous polytetrafluoroethylene without discernible node and fibril microstructure and (wet) stretched PTFE layer having low or substantially no fluid permeability that includes a closed cell microstructure having high density regions whose grain boundaries are directly interconnected to grain boundaries of adjacent high density regions and having substantially no node and fibril microstructure, and porous PTFE having no or substantially no fluid permeability. PTFE layers lacking distinct, parallel fibrils that interconnect adjacent nodes of ePTFE and have no discernible node and fibril microstructure when viewed at a scanning electron microscope (SEM) magnification of 20,000. A porous PTFE layer having no or substantially no fluid permeability may have a Gurley Number of greater than about 12 hours, or up to a Gurley Number that is essentially infinite, or too high to measure, indicating no measurable fluid permeability. Some PTFE layers having substantially no fluid permeability may have a Gurley Number at 100 cc of air of greater than about $10^6$ seconds. The Gurley Seconds is determined by measuring the time necessary for a given volume of air, typically, 25 cc, 100 cc or 300 cc, to flow through a standard 1 square inch of material or film under a standard pressure, such as 12.4 cm column of water. Such testing may be carried out with a Gurley Densometer, made by Gurley Precision Instruments, Troy, N.Y. Details of such useful PTFE materials and methods for manufacture of the same may be found in commonly owned U.S. Patent Application Publication No. 2006/0233991, the contents of which are incorporated herein by reference in their entirety.

Figure 6:
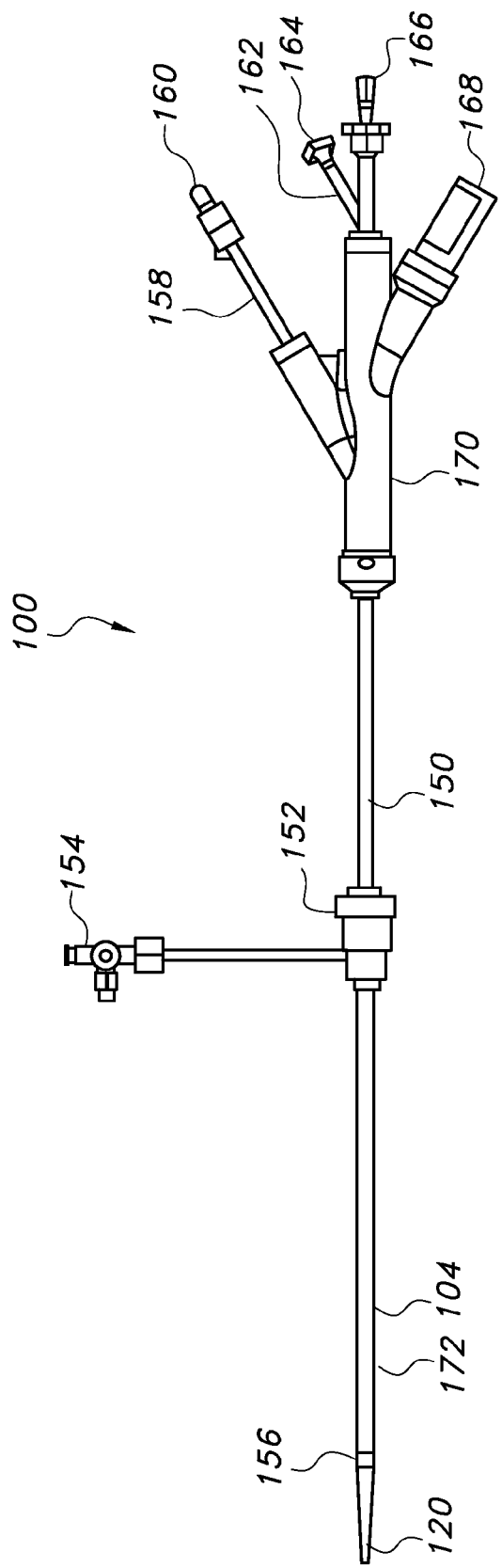
FIG. 6 is a side elevational view of the endovascular delivery system of the present invention.

FIG. 6 is a side elevational view of the endovascular delivery system 100 of the present invention. The endovascular delivery system 100 may include, among other things, the nosecone 120; the outer sheath 104; a retraction knob or handle 152 for the outer sheath 104; a flush port 154 for the outer sheath 104; an outer sheath radiopaque marker band 156; an inner tubular member 150; an inflation material or polymer fill connector port 158; an inflation material or polymer fill cap 160; a guidewire flush port 162; a guidewire flush port cap 164; a guidewire port 166; and nested stent release knobs 168; interrelated as shown.

The flush port 154 for the outer sheath 104 may be used to flush the outer sheath 104 during delivery stages. The outer sheath 104 may have a radiopaque marker band to aid the practitioner in properly navigating the delivery system 100 to the desired bodily site. The outer sheath 104 is retractable by movement of the retraction knob or handle 152 for the outer sheath 104 by a practitioner towards the proximal handle assembly 170 of the delivery system 100. The inner tubular member 150 is disposed from the inner tubular member 150 toward a proximal portion of the delivery system 100. The inflation material or polymer fill connector port 158 and the inflation material or polymer fill cap 160 are useful for providing inflation material or polymer fill material to inflate proximal inflatable cuffs 134 and the network of inflatable channels 136 of the inflatable graft 114. The guidewire flush port 162 and the guidewire flush port cap 164 are useful for flushing the guidewire port 166 during delivery stages of the delivery system 100. The nested stent release knobs 168 contains a series of nested knobs (not shown) that that are used to engage release mechanisms for delivery of the endovascular prosthesis 106. Further details, including but not limited to methods, catheters and systems, for deployment of endovascular prostheses are disclosed in commonly owned U.S. Pat. Nos. 6,761,733 and 6,733,521 and commonly owned U.S. Patent Application Publication Nos. 2006/0009833 and 2009/0099649, all of which are incorporated by reference herein in their entirety.

Figure 7:
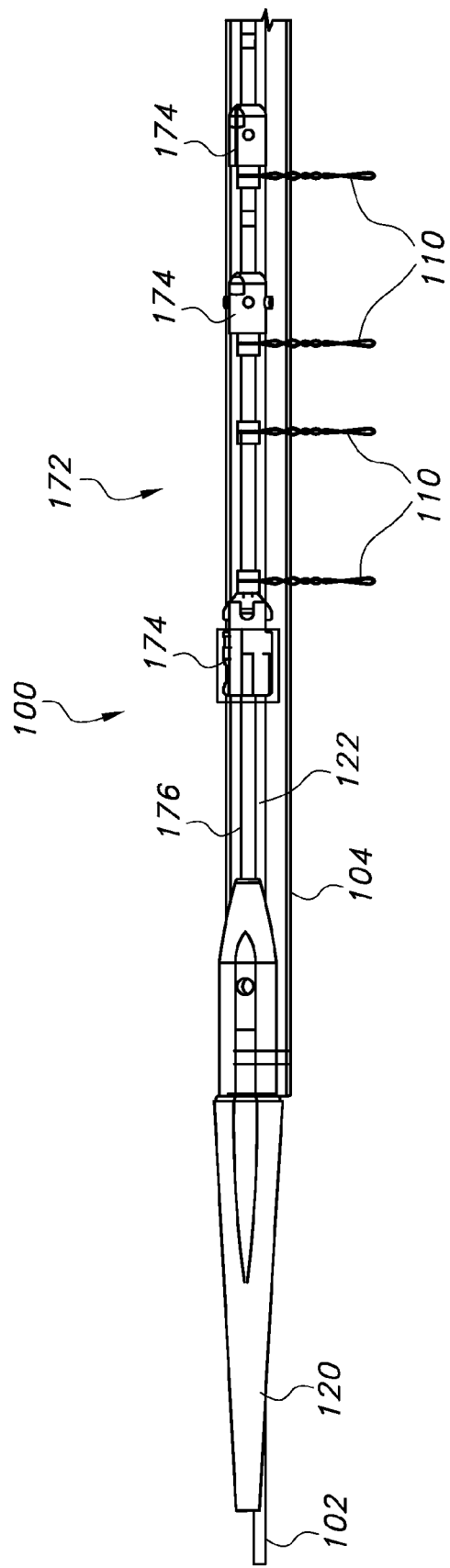
FIG. 7 is a side elevational and partial cutaway view of the distal portion of the endovascular delivery system of the present invention.
Figure 8:
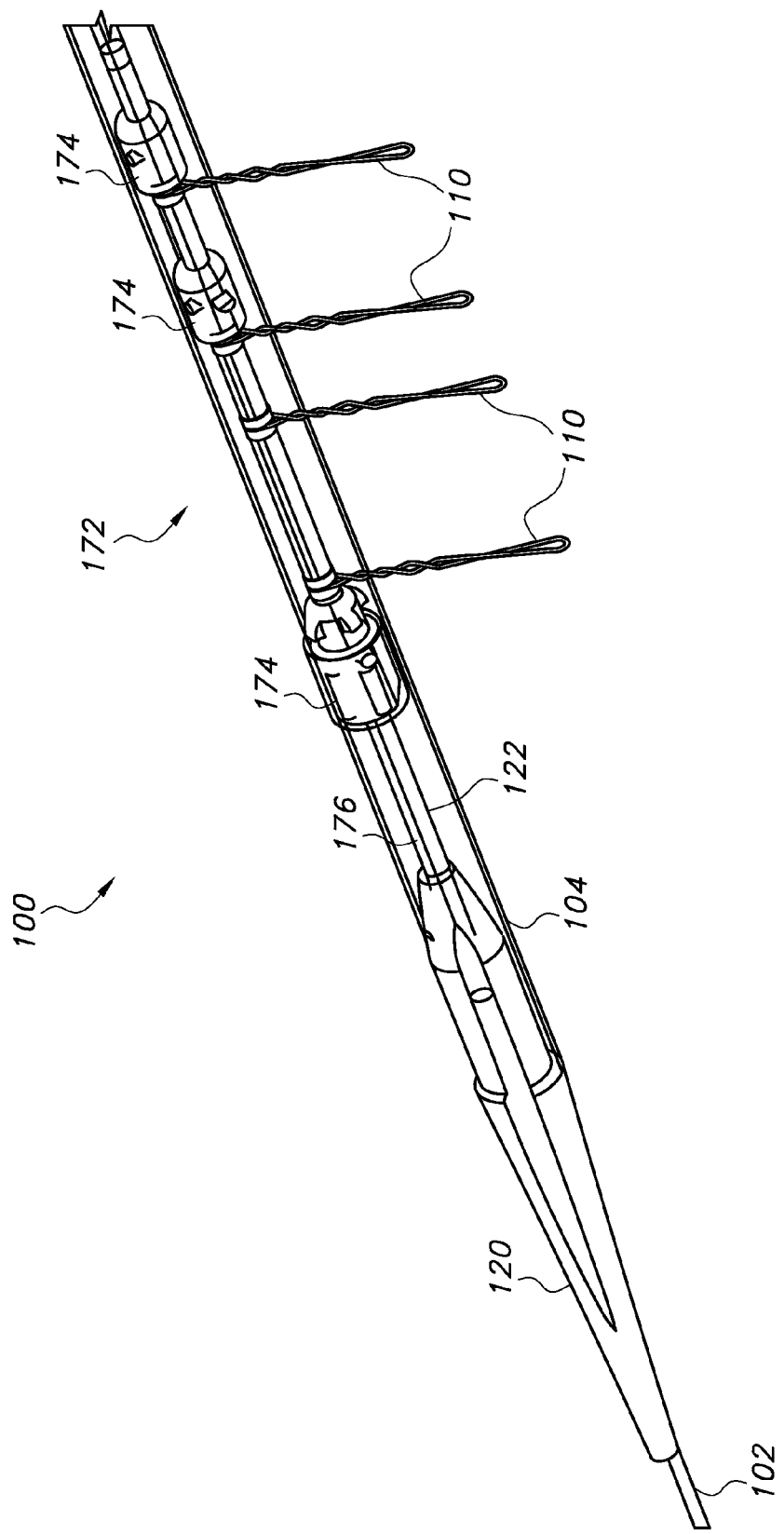
FIG. 8 is a partial perspective and partial cutaway view of the distal portion of the endovascular delivery system of the present invention.

FIG. 7 is a side elevational and partial cutaway view of the distal portion 172 of the endovascular delivery system 100 of the present invention, and FIG. 8 is a partial perspective and partial cutaway view of the distal portion 172 of the endovascular delivery system 100 of the present invention. The distal portion 172 of the endovascular delivery system 100 includes a prosthesis/stent holder 174 disposed upon a prosthesis/stent holder guidewire 176. The holder 174 is useful releasably securing the endovascular prosthesis 106 (not shown) within the delivery system 100. The holder 174 inhibits or substantially inhibits undesirable longitudinal and/or circumferential movement of the endovascular prostheses 106 during delivery stages of the delivery system 100. Belts 110 serve to restrain the endovascular prosthesis 106 in a radially constrained stage until desired release of the endovascular prosthesis 106.

During delivery of the prosthesis 106, the physician implanting the device will insert the device into the patient, using a series of radiopaque markers to align the prosthesis in the appropriate location. Typical delivery devices, however, sometimes use radiopaque markers in the prosthesis itself to aid in proper placement of the device in the body. Use of radiopaque markers in the prosthesis itself can be insufficient due to the inherent radiopacity of some prostheses that makes identification and differentiation of such radiopaque markers difficult.

Figure 9:
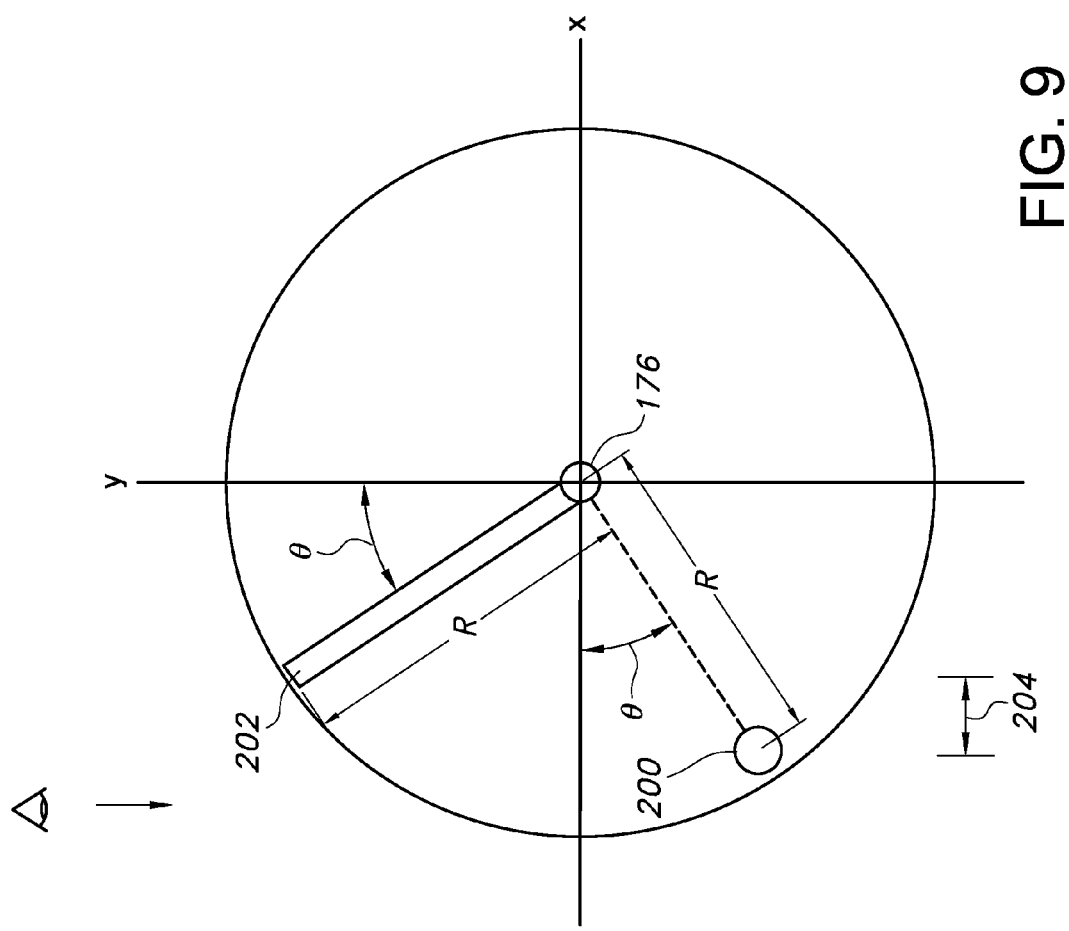
FIG. 9 is a schematic representation of the angles formed during rotation of a delivery system using only one axially aligned radiopaque marker.

FIG. 9 demonstrates an advantage of an embodiment of the current invention that includes two markers 200 and 202, which can be radiopaque. FIG. 9 is a cross sectional schematic view of a prosthesis delivery device along a longitudinal axis of guidewire 176, showing a first marker 200 and a second marker 202. During delivery of a prosthesis using this embodiment, the physician implanting the device typically views one or more images of the prosthesis and its delivery system, including markers 200 and 202, via fluoroscopy, which provides an image of the delivery system from a perspective that is generally perpendicular to the longitudinal axes of the delivery system and guidewire 176, as seen by the depiction of an eyesight in FIG. 9. As depicted in the FIG. 9 schematic, the direction of eyesight is along the axis y. Guidewire 176 may be made of a radiopaque material. As can be seen, there is a gap 204 as seen in the projection in the view along the y axis between the first marker 200 and the second marker 202. In perfect axial/rotational alignment with the line of sight of the user (i.e., wherein a rotational angle θ, defined as that angle formed between marker 200 or 202 and either an x or y axis, as seen in the FIG. 9, is defined to be zero), the gap 204 is at its maximum. As can be seen in FIG. 9, as the device is rotated along the guidewire 176 longitudinal axis away from this position, the gap 204 becomes smaller. The radial separation of each marker 200, 202 (in the case of marker 202, it being the radial separation as measured to the outermost portion from guidewire 176), is depicted with the symbol "R". The gap 204 between the first marker 200 and second marker 202 is denoted as R cos θ-R sin θ. Notably, without a second marker 202, the gap is denoted as R cos θ (ignoring the small effect of the width of guidewire 176).

To allow the physician to achieve the most precise desired rotational/circumferential alignment of the prosthesis at the intended θ=0 position, gap 204 may be as large as possible. Thus, during delivery of the prosthesis, the physician implanting the device may rotate the prosthesis until the gap between the markers is at its largest. Vascular bodies within an individual may not have perfect symmetry along the guidewire 176 axis, or alternatively, along the axis of the catheter lumen, and a vascular prosthesis may be configured accordingly. As such, the placement of a prosthesis within these vascular bodies may require precise and accurate rotational alignment; that is, alignment of the device circumferentially along its longitudinal axis. Even a small misalignment may result in defective placement within the vascular body or complicate and/or lengthen the delivery procedure, which could result in negative clinical outcomes and/or increased costs associated with the procedure. For example, cannulation of the contralateral limb aperture (gate) may be adversely affected if the device is not oriented properly. Proper orientation of the device, for example, allows the aortic body limbs to be positioned laterally, facilitating access to the contralateral gate via a guidewire/catheter inserted into the patient's contralateral access vessels.

With respect to second marker 202 of the embodiment depicted in FIG. 9, the rate of change of gap 204 as a function of rotational angle of the catheter can be denoted as the "gap equation":

$$d_{gap}/d\theta = -R(\sin\theta + \cos\theta),$$

while in the case of a system without a second marker as configured in embodiments described herein the rate of change of the gap can be denoted as:

$$d_{gap}/d\theta = -R \sin\theta.$$

For some embodiments, when the prosthesis 106 is positioned correctly for optimum deployment (θ is approximately zero), $d_{gap}/d\theta$ is about −R, a relatively large value which indicates a strong sensitivity to gap width as a function of rotational angle (in contrast, for the case of a system containing a single marker, $d_{gap}/d\theta=0$; i.e., there is no variation or sensitivity of gap 204 width to rotational angle θ). For a situation in which a small angular error exists; for example, if θ is about 0.1 radians (about 6° rotated), then $d_{gap}/d\theta$ is approximately 11 times greater with embodiments containing two markers as compared to systems containing a single marker case.

Accordingly, some embodiments contain at least one, and desirably two, additional markers, each disposed approximately at a +/−90° angle from a first marker as measured from the longitudinal axis of guidewire 176. Although the Figures show axially aligned tubular markers, useful markers may simply be dots, squares, or bars that radiate from the center of the device. Desirably, the markers are oriented as far away from the center of the device as possible, to maximize the gap between the axis (and thus the guidewire) and the marker. In embodiments that use two or three such markers, each offset by approximately 90° relative to a first marker as described above, greater than eleven times the rotational sensitivity to the gap may be afforded to the physician implanting the prosthesis, thus allowing significantly more control in the alignment of the prosthesis during implantation. Such embodiments solve or mitigate problems with systems having a single marker as outlined above, because by virtue of the additional markers being offset by approximately 90° at least one of the markers will always be in a position to contribute high rotational angle sensitivity during the prosthesis implantation procedure (i.e., either the sin θ or cos θ term in the "gap equation" will be operative). This allows the physician to have improved prosthesis placement sensitivity during its implantation, and particular, increased placement sensitivity when performing any rotational maneuvers during the implantation procedure.

An improved radiopaque marker system may be useful for the user to accurately deliver a prosthesis. The device may include a series of markers, as will be described below. The description below includes a series of markers in one component of the delivery system, specifically the prosthesis holder. However, it will be understood that the marker system described herein may be useful in any portion of the delivery system, including, for example, the sheath or nosecone. In addition, the delivery system may include a separate component including the marker system and the purpose of this separate component is to provide the marker system to the delivery system.

Figure 10:
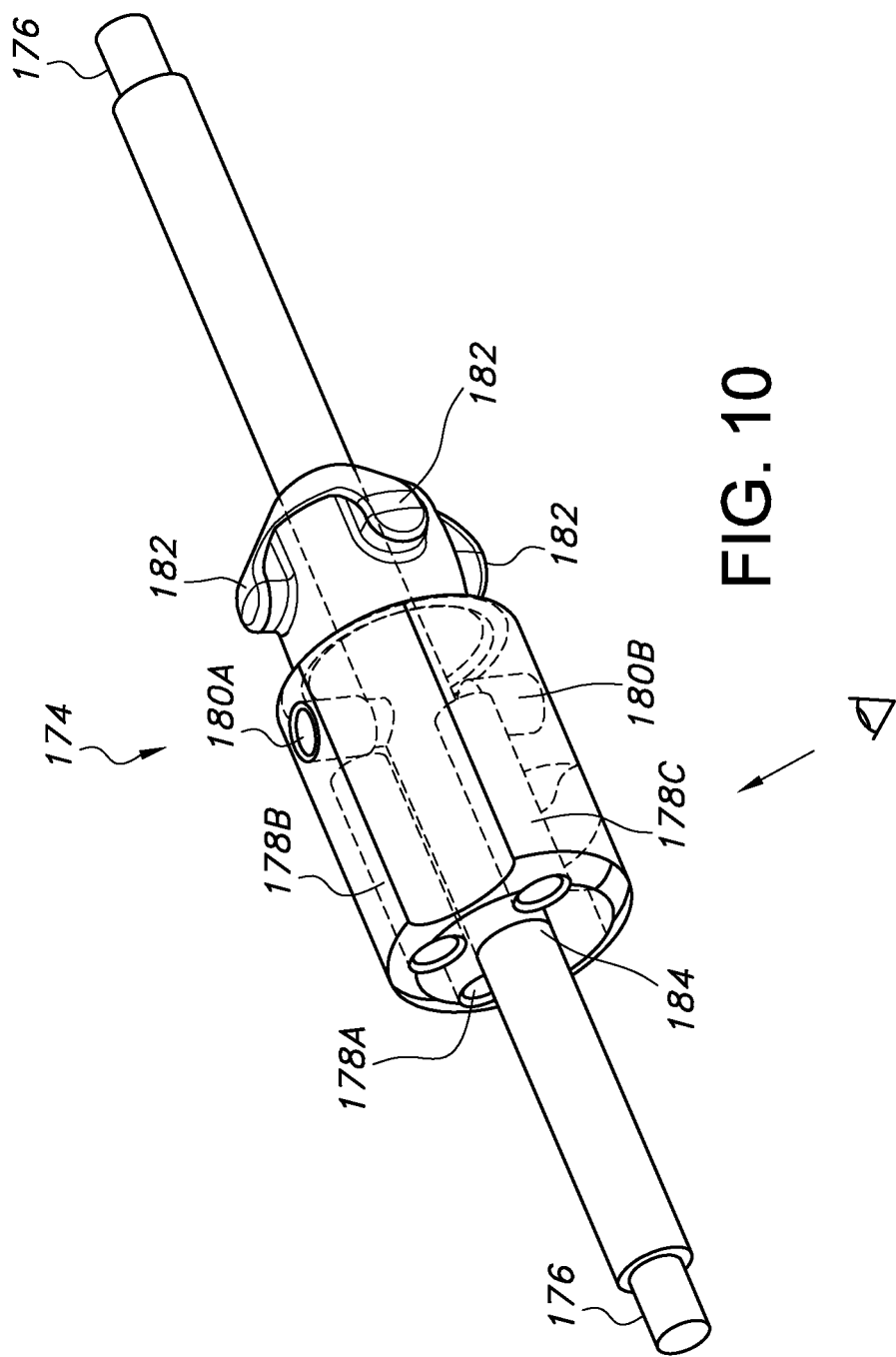
FIG. 10 is a rear perspective view of the prosthesis holder having an improved radiopaque marker system of the present invention.

FIGS. 10-17 show an embodiment of an improved radiopaque marker system as described herein. FIG. 10 shows a rear and front perspective view of components of the system, respectively. A prosthesis/stent holder guidewire 176 extends through a central lumen 184 disposed in prosthesis/stent holder 174, thus forming a longitudinal axis of lumen 184 that is coincident with a longitudinal axis of guidewire 176 when so configured. Further, in the embodiment depicted in FIG. 10, the prosthesis/stent holder guidewire 176 fully extends through the prosthesis/stent holder lumen 184 such that the prosthesis/stent holder guidewire is exposed at each end of the prosthesis/stent holder 174.

Guidewire 176 may be made of any desired material. In one embodiment, guidewire 176 is made from a material that is viewable via radiography, fluoroscopy or other visualization techniques. For example, such materials may be metal, such as palladium, iridium, gold, tantalum, tungsten, platinum, and combinations thereof. The material may be a polymeric material, such as a radiopaque nylon. Alternatively, the material may include fillers that are radiopaque, such as bismuth, barium, and tungsten. Although the present invention contemplates using a guidewire 176 to aid in placement of the prosthesis, the use of the guidewire 176 for final placement is optional. That is, the guidewire 176 could be retracted, or not used at all, and the markers in the prosthesis/stent holder 174 can be used to provide guidance as to the proper rotational alignment of the prosthesis.

Within the body of the prosthesis/stent holder 174 of the embodiment shown in FIG. 10, there is a series of three axially aligned markers 178A, 178B, 178C, which are all parallel to the axis formed by the axial guidewire 176. Although the three axially aligned markers 178A, 178B, 178C are depicted in the Figures as being generally cylindrical, it is understood that any suitable markers may be used, including, for example, dots or a series of dots, or bars. The three axially aligned markers 178A, 178B, 178C are positioned at approximately 90° intervals around the circumference of the prosthesis/stent holder 174 and separated from the prosthesis/stent holder guidewire 176 by a suitable known distance. The three axially aligned markers 178A, 178B, 178C in some embodiments are each of the same length and the same diameter, although some variation in sizing may occur. Further, each of the three axially aligned markers 178A, 178B, 178C are separated from the prosthesis/stent holder guidewire 176 by the same distance, thus creating the same gap size therebetween.

Markers 178A, 178B, 178C may be made from any desired material visible with imaging modality used in a deployment procedure, including a radiopaque material, such as platinum, iridium, palladium, gold, tantalum, tungsten, radiopaque nylon, bismuth, barium, tungsten or combinations thereof. In some embodiments, each of the three axially aligned markers 178A, 178B, 178C are made from the same material, although it is not necessary. In one particular embodiment, markers 178A, 178B, 178C are made from a combination of 90% by weight platinum and 10% by weight iridium. Markers 178A, 178B, 178C may be the same or different shape, and may be cylindrical as shown in FIG. 10; however, any other suitable symmetric or asymmetric shape may be used for one or more of the markers, including, for example, rectangular prisms, bars, cubes, spheres, split cylinders and half-moon shapes. One or more of markers 178A, 178B, 178C may be of a hollow, partially hollow, or solid construction. In addition, there may be one physical marker, which has separate elements secured to each other and spaced apart to create a gap between elements. In addition, there may be more than three markers, so long as there is at least two elements disposed approximately 90° from each other. For example, there may be more than four or five markers in the device. In addition, the markers may be a series of discontinuous markers, such as spheres or cubes, which create the ability to view the gap 186 upon rotation of the device.

In embodiments using a guidewire 176, diameter D176 of the prosthesis/stent holder guidewire 176 may be equal to or larger than the diameter D178A, D178B, D178C of each of the three axially aligned markers 178A, 178B, 178C. Thus, during implantation, if the device is properly aligned relative to its intended transverse viewing direction, the two side axially aligned markers 178A, 178C will be visually superimposed along with the guidewire 176, and a maximum gap will be visible between collinear markers 178A, 178C and center marker 178B. In some embodiments, the diameter of the prosthesis/stent holder guidewire 176 may be from about 0.010 inches to about 0.060 inches, or approximately 0.030 to about 0.050 inches, and the diameter of each of the three axially aligned markers 178A, 178B, 178C is approximately 0.010 inches to about 0.060 inches, or approximately 0.020 inches to about 0.030 inches.

The prosthesis/stent holder 174 may optionally include one or more than one markers 180A, 180B which may be radiopaque and are disposed such that their axial length along a direction that is approximately 90° (perpendicular) to the axis of the prosthesis/stent holder guidewire 176. These markers 180A, 180B may be made from the same material as the three axially aligned markers 178A, 178B, 178C and/or the prosthesis/stent holder guidewire 176, or may be made from a different radiopaque material. Markers 180A, 180B may be cylindrical in shape, but may take any desired shape as described for markers 178A-C. Inclusion of markers 180A, 180B is optional, as they further aid in the alignment of the prosthetic device.

The prosthesis/stent holder 174 in the embodiment shown in FIGS. 10-17 includes a series of crown anchors 182 that secure the prosthesis/stent in place before and during implantation. The crowns of the prosthetic stent (not shown) may be secured around the crown anchors 182, thus preventing rotational movement of the stent before and during implantation. The prosthesis/stent holder 174 and crown anchors 182 may be made from any desired material, including a non-radiopaque material to allow a physician to more readily visualize the radiopaque markers and the guidewire 176 during implantation.

Markers 178A, 178B, 178C, 180A and 180B may be formed and assembled into the system by any suitable means. One or more of the markers may be press fitted into the prosthesis/stent holder 174; alternatively, one or more of the markers may be molded into the prosthesis/stent holder 174, so that they are fully or partially encapsulated within the material comprising holder 174. In some embodiments, one or more of the markers may be press fitted and secured with a suitable adhesive, such as a UV or cyanoacrylate adhesive.

Figure 11:
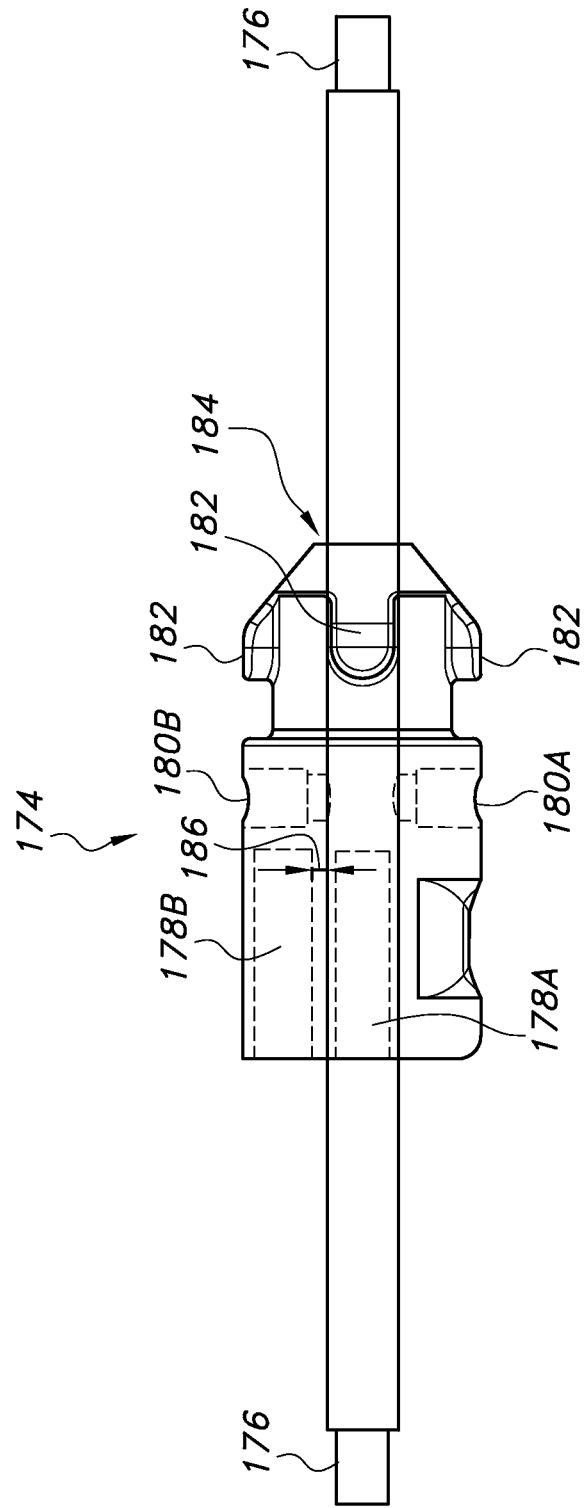
FIG. 11 is a side view of the prosthesis holder of the present invention.

FIG. 11 shows a side view of the prosthesis/stent holder 174 of the embodiment shown in FIG. 10. The side view of FIG. 11 is at a viewing angle whereby the longitudinal axes of markers 178A and 178C are visually aligned in an overlapping manner with the longitudinal axis of guidewire 176 disposed within lumen 184 of holder 174. This view may be, for example, a view that a physician will have when implanting the prosthesis in the vasculature under, e.g., fluoroscopy. For purposes of describing features of this embodiment, one may consider this a baseline configuration in which there has been no rotation of the prosthesis/stent holder 174 relative to the line of sight of the user, indicated in FIGS. 10 and 13 (that is, θ is zero).

In the FIG. 11 view, a gap 186 is visible between an outer surface or circumference of the second axially aligned marker 178B and the surface of prosthesis/stent holder guidewire 176. The projection of the gap 186 as viewed by the user along the sight of axis y is measured between the outer surface or circumference of the guidewire 176 and the outer surface of the second axially aligned marker 178B. As explained above, during the prosthesis implantation procedure under visualization such as fluoroscopy, when the system is rotated such that this projection of the gap 186 is maximized so that the physician will be able to tell that the prosthesis is in the desired rotational alignment. Also, as can be seen, when the device is rotated as shown in the view of FIG. 11, markers 178A, 178C are visually aligned with the prosthesis/stent holder guidewire 176 such that they largely or completely overlap. Under fluorescopy, then, markers 178A, 178C cannot readily be seen in this alignment, since the guidewire 176 is wider than the markers 178A, 178C in this particular embodiment.

In the rotational configuration shown in FIG. 11, gap 186 is at its largest. The gap 186 as viewed by the user in this configuration may be as large as possible, which is dependent upon the size of the catheter used. In order to maximize the gap 186, the marker diameter D178 may be kept to as minimum as possible while still allowing the user to view the marker 178 via imaging device. If the material from which the markers 178 are made is extremely radiopaque, a smaller or thinner marker 178 may be used and still provide the user with visibility with an imaging device. A radiopaque marker 178 may have a diameter of from about 0.010 inches to about 0.050 inches, or from about 0.020 inches to about 0.040 inches. For example, depending upon the radius of the catheter, the gap may have a size of about 0.010 to about 0.080 inches. A gap space for typical prosthetic systems such as those described herein may be from about 0.020 to about 0.065 inch, or may be from about 0.035 to about 0.055 inches. However, a larger gap may be used to provide the user with ease of viewing even with lower quality imaging systems or less radiopaque materials.

Figure 12:
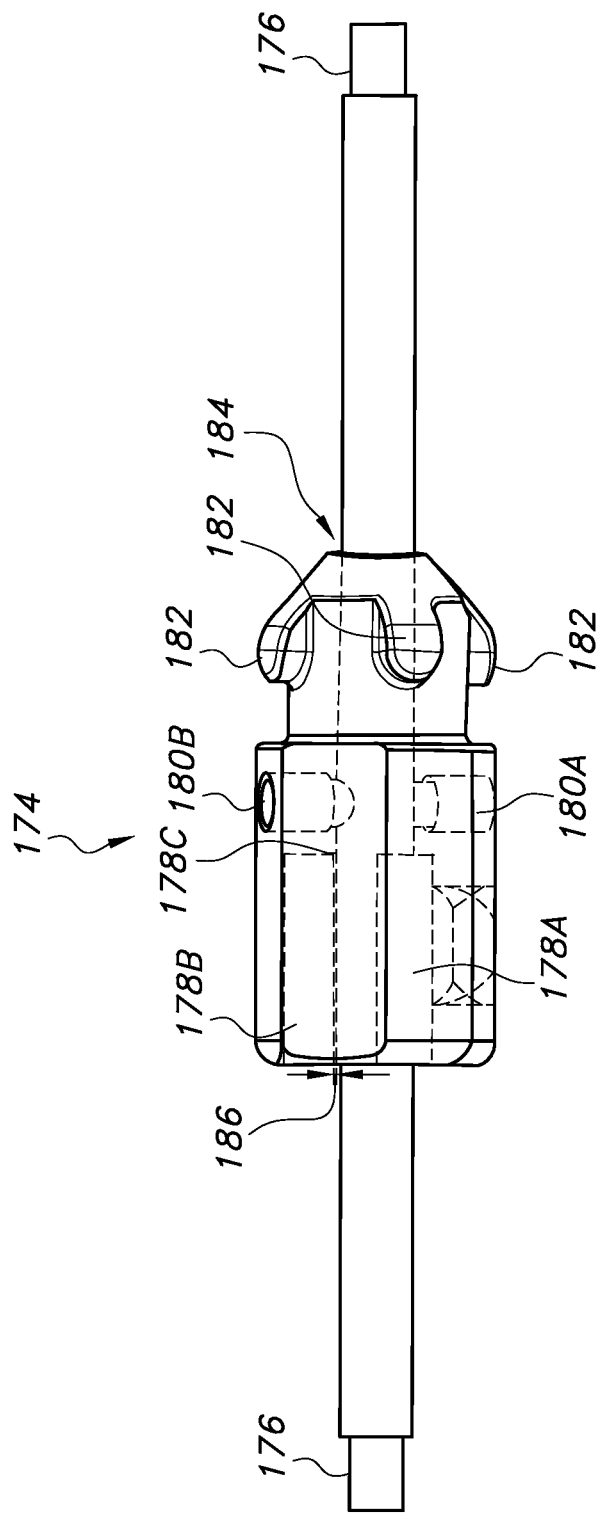
FIG. 12 is a side view of the prosthesis holder of the present invention, which has been rotated along its axis.

FIG. 12 shows the system of FIG. 11 that has been rotated in a clockwise direction about guidewire 176 longitudinal axis by approximately 10°. As can be seen, markers 178A, 178B, 178C have all now been rotated clockwise. A portion of marker 178C would now be visible in this view under, e.g., fluoroscopy, as extending slightly above the boundary or outer surface of guidewire 176. Similarly, a portion of marker 178A would now be visible as extending in this view slightly below the boundary or outer surface of guidewire 176. Marker 178B now appears to be closer to the guidewire 176 when viewed from this angle as the length of gap 186 is now smaller compared to its length in the direct alignment view of FIG. 11. Due to the presence of both the first axially aligned marker 178A and the second axially aligned marker 178B, the gap 186 is affected to a greater degree even with a small rotation of the prosthesis/stent holder 174. This greater reduction in gap 186 size during rotation of the device compared to systems with a single marker or a different configuration allows for greater precision during implantation. In addition, through the use of three markers 178A, 178B, 178C, the gap 186 may be minimized whether the device is turned in the clockwise or counterclockwise direction.

Figure 13:
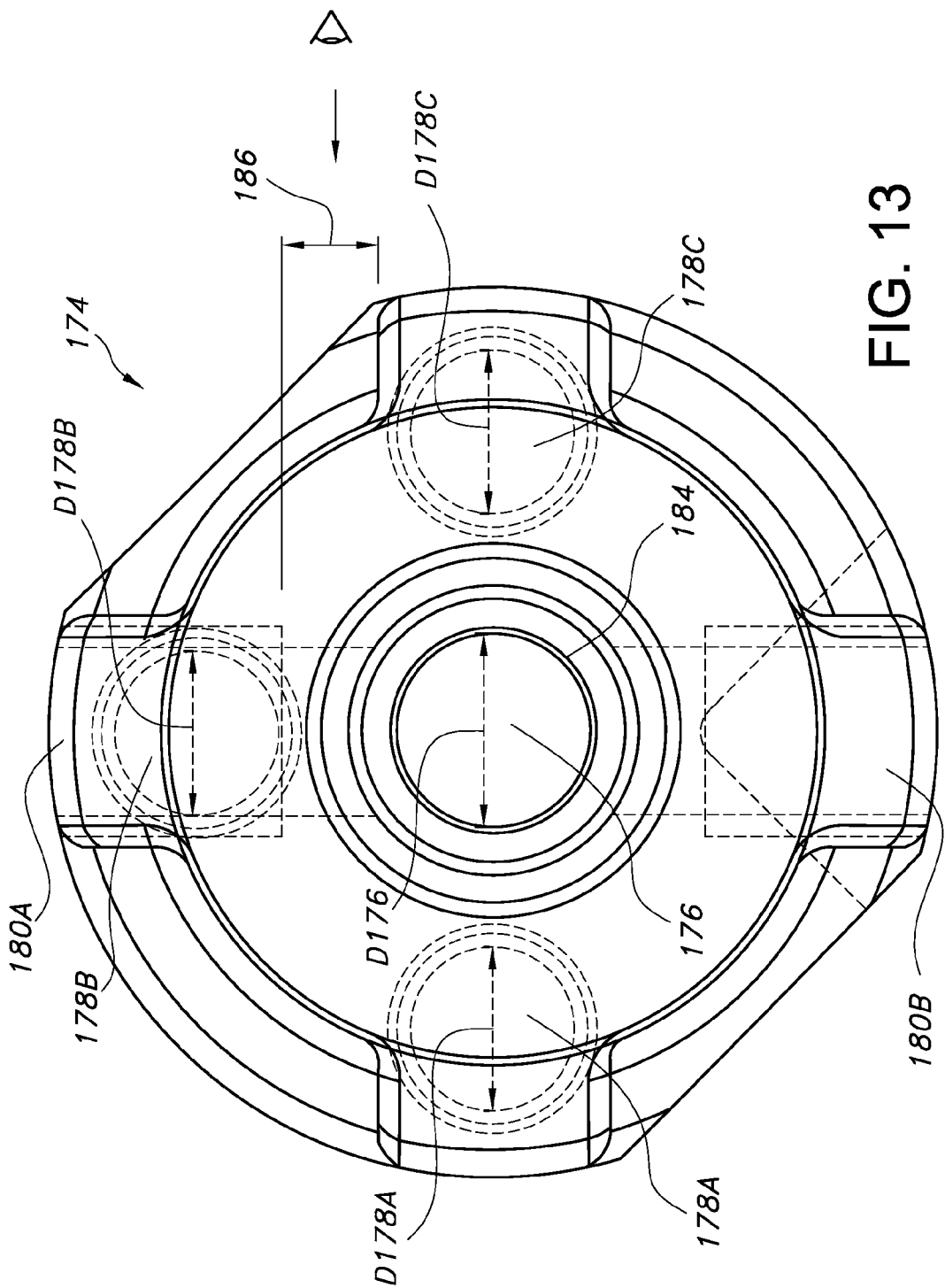
FIG. 13 is an axial view of the prosthesis holder of the present invention

FIG. 13 shows a view of the prosthesis/stent holder 174 transverse to its longitudinal axis and longitudinal axis of its lumen 184 and the coincident longitudinal axis of guidewire 176 (extending in a normal direction out of the plane of the page). As can be seen and as previously described with respect to FIG. 10, guidewire 176 extends through lumen 184 of the prosthesis/stent holder 174. Also as previously described, three axially aligned markers 178A, 178B and 178C are disposed around the guidewire 176, which may be spaced at approximately 90° intervals and at an equal distance from the guidewire 176. Projection of the gap 186, described with respect to the views of FIGS. 11 and 12, is also shown.

Figure 14:
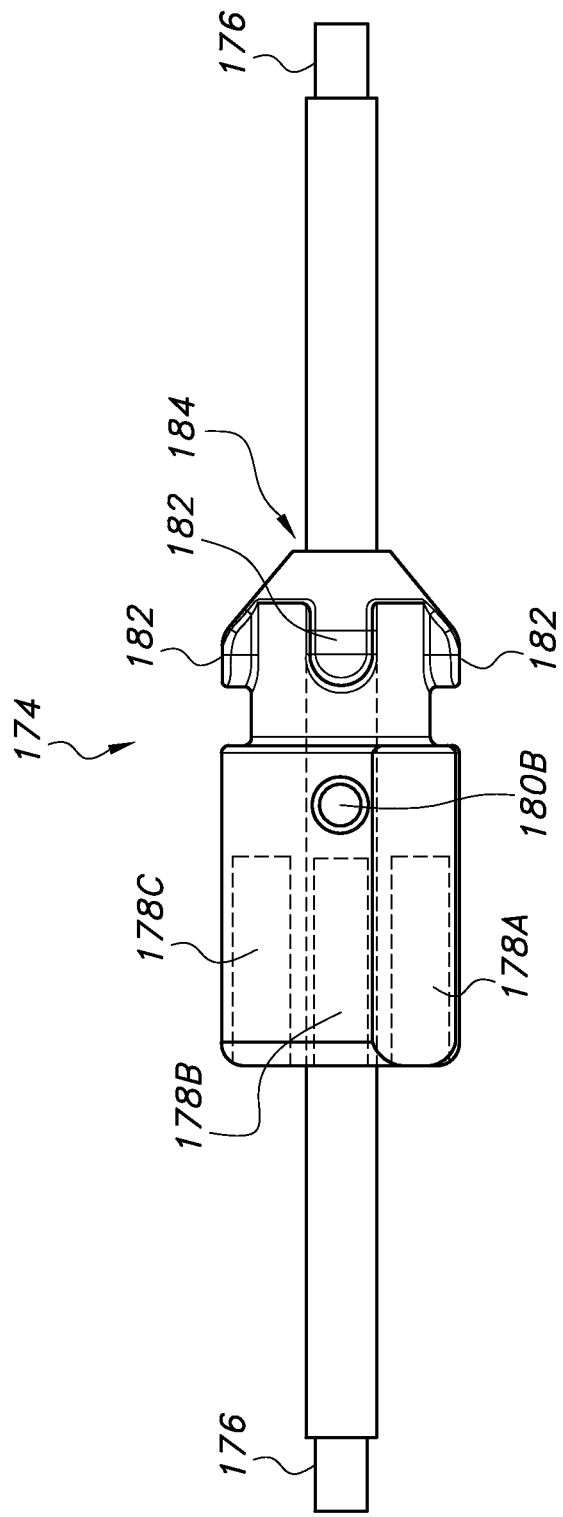
FIG. 14 is a top view of the prosthesis holder of the present invention.
Figure 15:
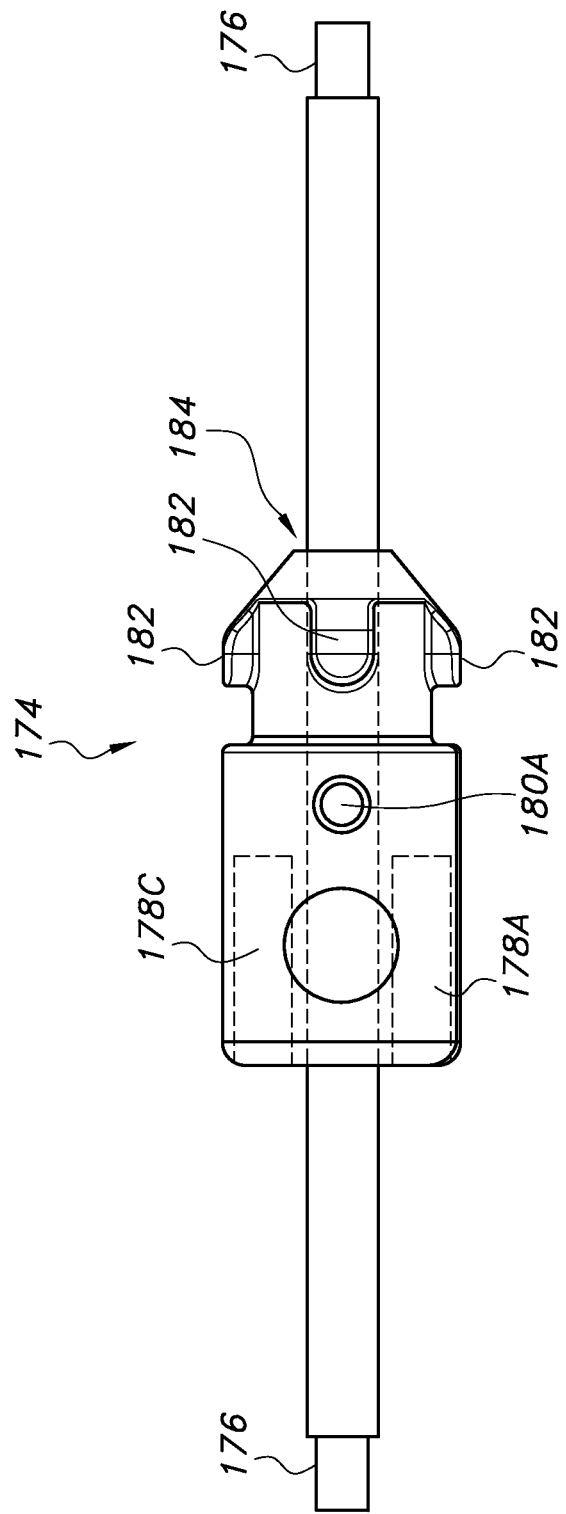
FIG. 15 is a bottom view of the prosthesis holder of the present invention.

FIG. 14 shows the prosthesis/stent holder 174 as viewed from the top and FIG. 15 shows the prosthesis/stent holder 174 as viewed from the bottom (both relative to the orientation of the components in the FIG. 13 view). Notably, when viewed from the bottom, in direct alignment, the middle marker 178B, even if radiopaque, would be difficult or impossible to visualize by a deploying physician under, e.g., fluoroscopy, as it is shielded from view by a radiopaque guidewire 176.

Figure 16:
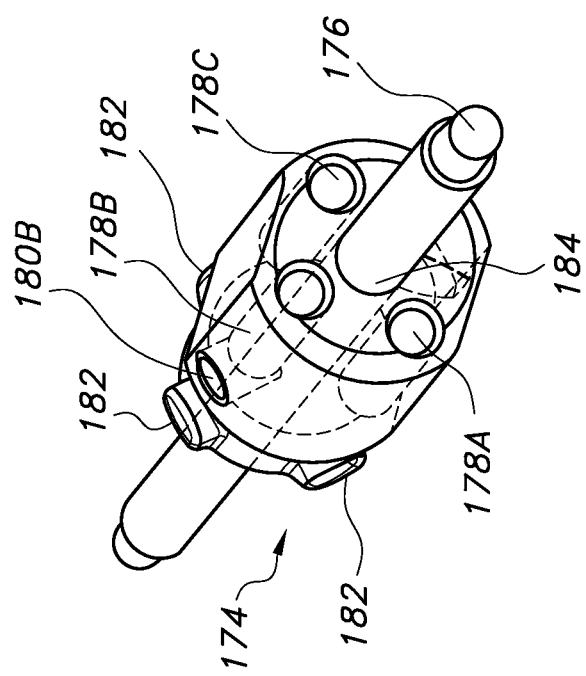
FIG. 16 is a rear perspective view of the prosthesis holder of the present invention.
Figure 17:
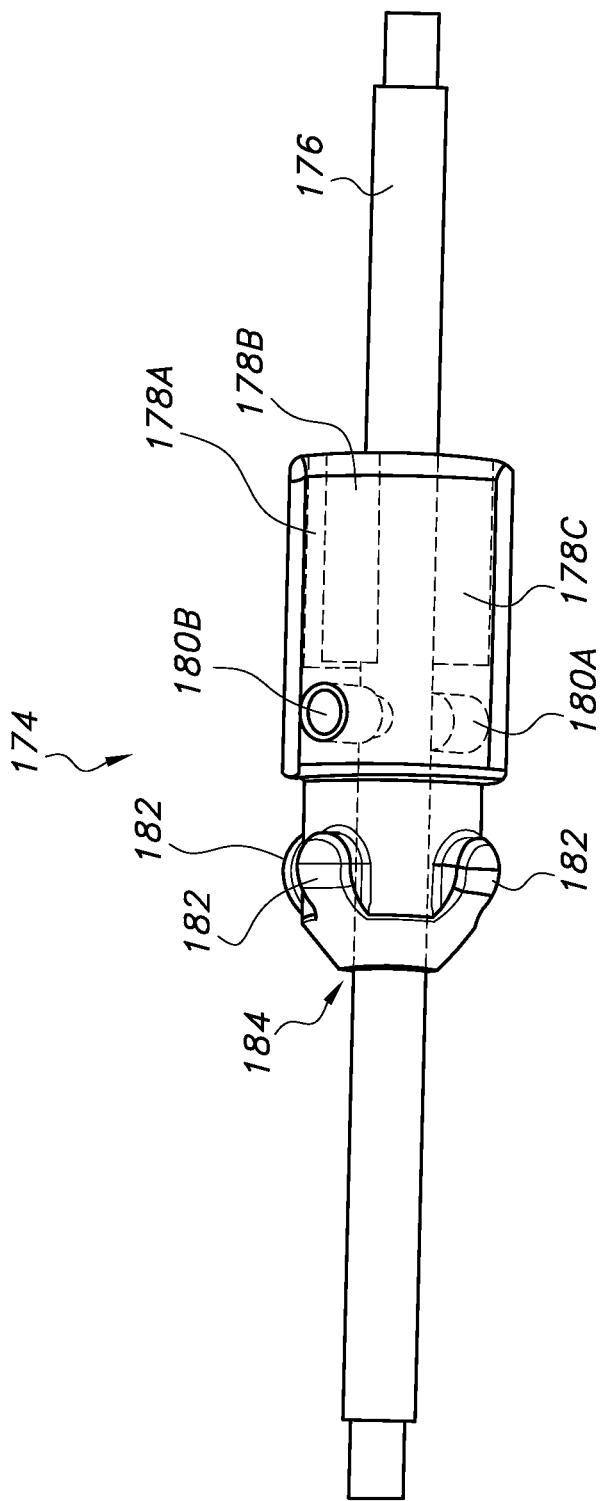
FIG. 17 is a side view of the prosthesis holder of the present invention, which has been axially rotated.

FIGS. 16 and 17 show a front perspective view and side view, respectively, after the prosthesis/stent holder 174 has been rotated slightly. As can be seen, the angles and gaps formed by the surface of guidewire 176 and the surfaces of axially aligned markers 178A, 178B, 178C are changed due to the rotation of the prosthesis/stent holder 174.

Figure 18:
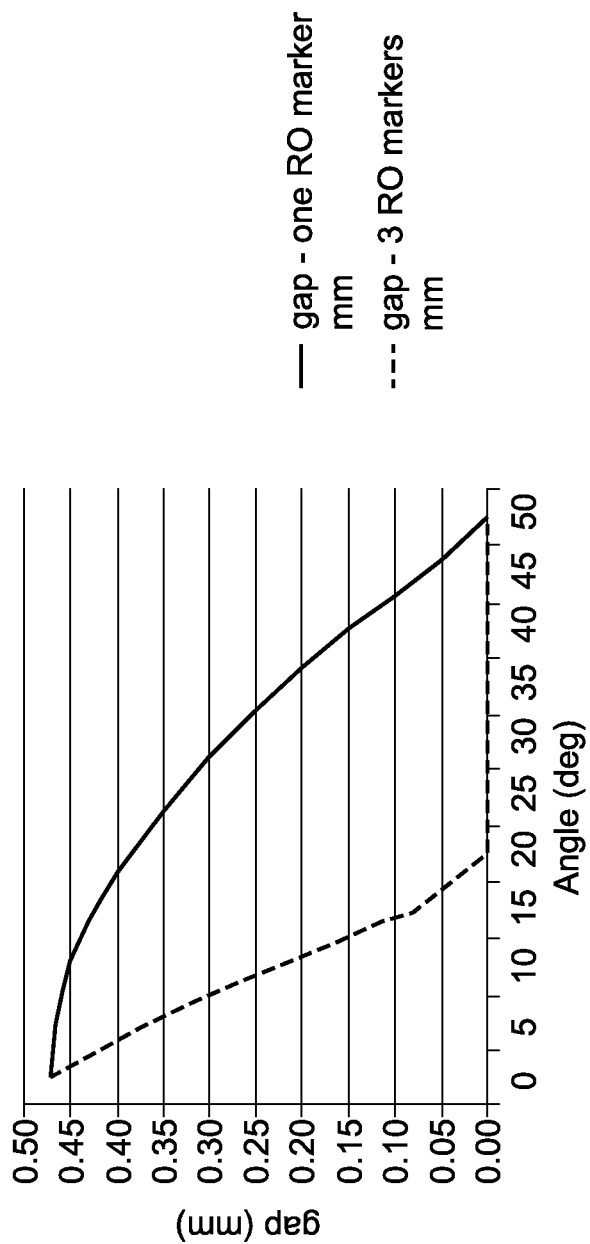
FIG. 18 is a chart depicting the improved gap spacing during rotation of the prosthesis.

FIG. 18 is a chart depicting the change in the gap 186 between the guidewire 176 and an axially aligned marker 178A, 178B, or 178C, depending upon the angle of rotation, as an embodiment of the prosthesis/stent holder 174 is rotated about its longitudinal axis. The chart shows the change in the gap (using three axially aligned markers 178A, 178B, 178C) as compared to the change of an identically-defined gap in a device that uses only one axially aligned marker (e.g., 178B) during identical rotation. As can be seen, in the inventive design, the size of gap 186 is reduced at a greater rate than in a device using one marker for a given angle of rotation. To reduce the gap 186 to approximately zero under visualization, the prosthesis/stent holder 174 need only be rotated about 22 degrees. In a device using only one axially aligned marker, however, the pro sthesis/stent holder need be rotated about 50 degrees. Thus, the inventive design provides a significantly greater degree of accuracy during rotation than other devices. Any shape or layout of markers 178A, 178B, 178C may be used, including, as explained above, continuous markers such as cylinders or discontinuous markers such as a series of dots, spheres, cubes, and the like. In addition, in one embodiment, different shaped markers may be used in the same device, to allow the user to be able to differentiate between the markers in the device and allow for even greater precision. For example, marker 178A can be a series of spherical dots, while marker 178C can be a series of cubes. As the device is rotated and the relative markers 178A, 178C can be seen by the user, the difference in shape may allow the user to have even greater control and precision.

The present invention may be used to deliver any desired devices, including stents, stent grafts, and the like. Bifurcated and fenestrated devices may be implanted using the present invention. The device may be used to aid in placement of devices in other locations, including, for example, in cranial implantation. Further, although the present invention is quite useful in aiding alignment when viewed from the side angle, the device may also be useful in providing alignment in axial or quasi-axial views. Various elements of the device create angles and gaps upon rotation when viewed from different angles, and thus the present invention may be useful in various other embodiments.

The inventive device has been explained with reference to the prosthesis/stent holder 174, but it is noted that the axially aligned marker system explained herein may be useful in other locations and other components of the delivery device.

In one embodiment, a device is prepared for implantation including the prosthesis/stent holder 174 described above, with a stent-graft prosthesis secured to the prosthesis/stent holder 174. The stent-graft prosthesis is secured to the prosthesis/stent holder 174 as explained above and the delivery device is prepared for implantation.

In some embodiments, a method of delivering and implanting a prosthesis is provided. In this embodiment, the delivery device, including prosthesis/stent holder 174 as explained above, is provided. The delivery device includes a prosthesis secured thereto, such as a stent-graft. The user, typically a physician, inserts the delivery device into the patient's body, more particularly, into the desired bodily lumen into which the prosthesis is to be implanted. The physician uses fluoroscopy to view radiopaque materials in the delivery device and prosthesis on a display device. As the device is being directed to its desired location, the physician views the location of the device via the display, which shows the presence of various radiopaque markers within the body.

When the prosthesis is at the desired location, the physician may then adjust the rotation of the device to ensure proper rotational/circumferential alignment. As explained above, there is a gap between the axially aligned radiopaque markers 178 and the prosthesis/stent holder guidewire 176. Using an anterior/posterior fluoroscopic view, for example, the physician rotates the prosthesis until the gap between the axially aligned radiopaque markers 178 and the prosthesis/stent holder guidewire 176 is at its largest and on the intended side of the guidewire 176. At this gap size, the prosthesis is in proper rotational alignment, and the prosthesis may be implanted with greater confidence that might otherwise be possible. After implantation, the delivery device is withdrawn. In embodiments where multiple prosthetic parts are being implanted together, one or more of the additional prosthetic parts may employ the improved radiopaque marker system as explained above, thereby ensuring proper rotational/circumferential placement of each prosthetic part.

Figure 19:
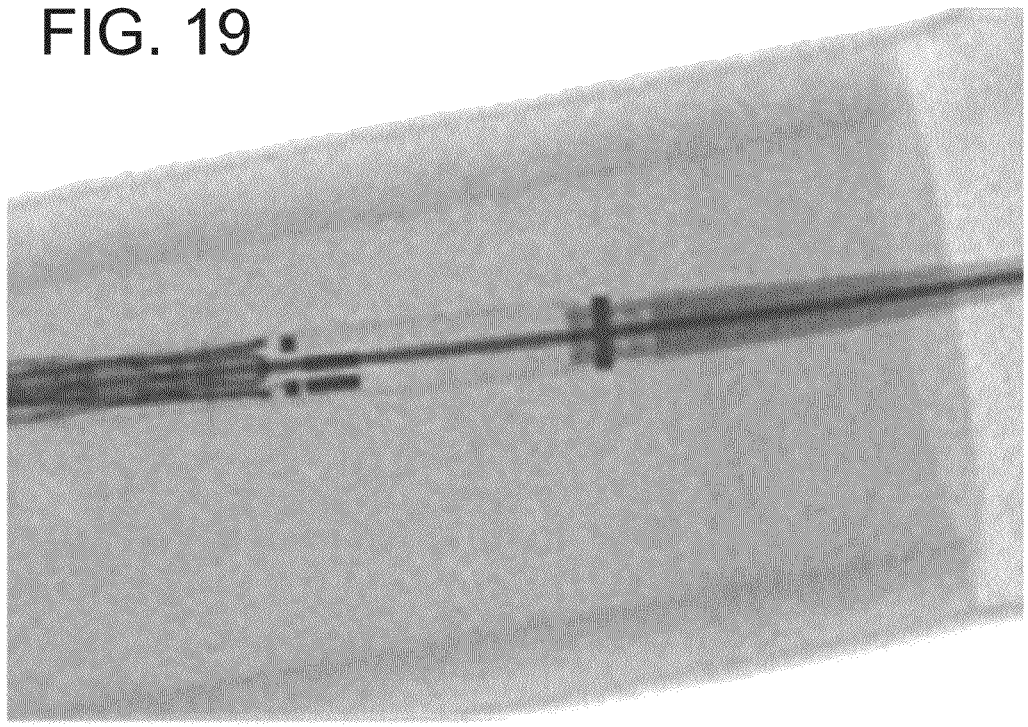
FIG. 19 is an image of one embodiment of the improved radiopaque marker system as seen under fluoroscopy in the ipsilateral right position.
Figure 20:
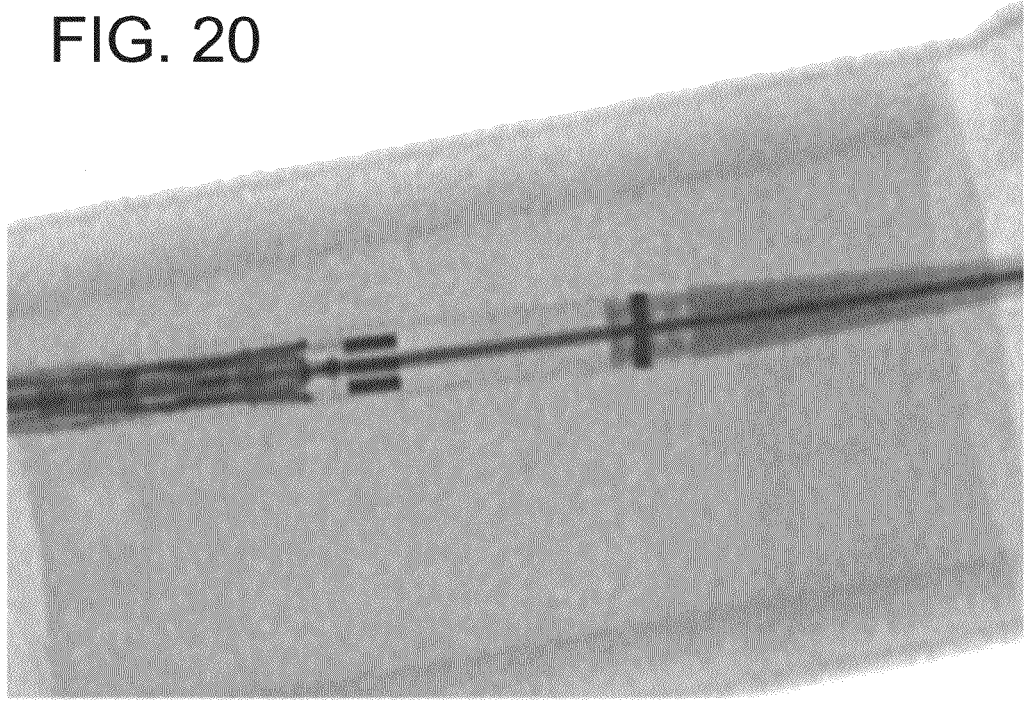
FIG. 20 is an image of one embodiment of the improved radiopaque marker system as seen under fluoroscopy in the anterior-posterior position.
Figure 21:
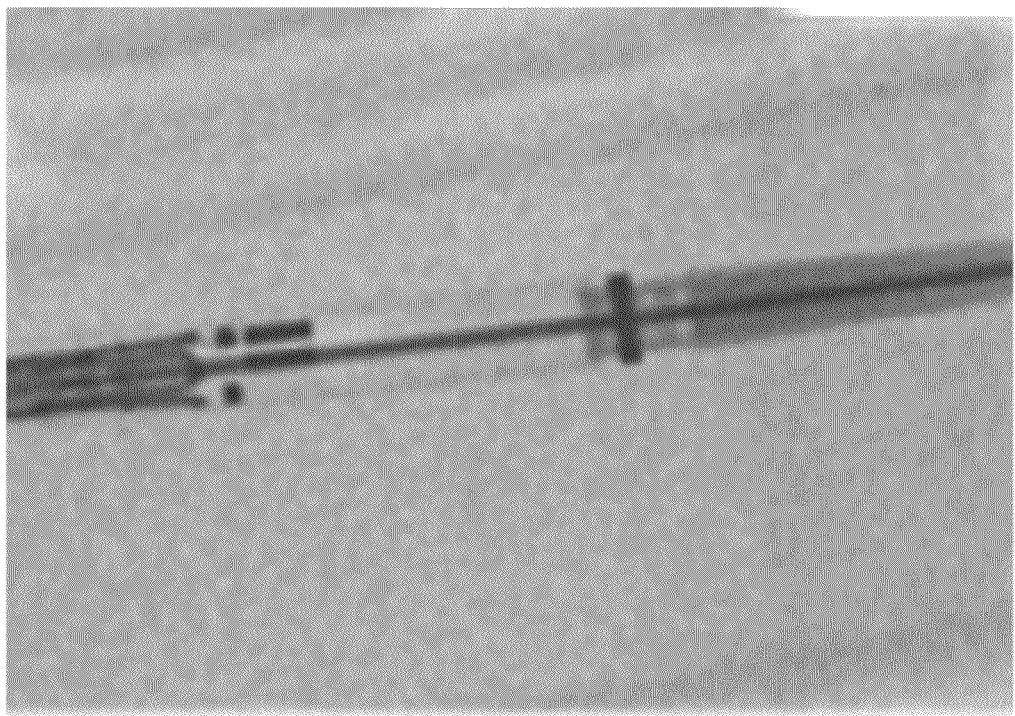
FIG. 21 is an image of one embodiment of the improved radiopaque marker system as seen under fluoroscopy in the ipsilateral left position.

FIGS. 19-21 show various positions of a radiopaque marker system of the present invention, as seen under fluoroscopy. FIG. 19 shows the device in the ipsilateral right position, FIG. 20 shows the device in the anterior-posterior position, and FIG. 21 shows the device in the ipsilateral left position. As can be seen in FIGS. 19 and 21, the middle marker is visible, while the two side markers are superimposed on the radiopaque guidewire. The two perpendicular markers are clearly visible. Also, as can be seen, there is a visible gap between the middle marker and the guidewire. FIG. 20 is oriented such that the middle marker is superimposed on the guidewire, while the two side markers are visible.

The following embodiments or aspects of the invention may be combined in any fashion and combination and be within the scope of the present invention, as follows:

Embodiment 1

An endovascular delivery system, comprising:
an elongate outer tubular device having an open lumen and opposed proximal and distal ends with a medial portion therein between;
a prosthesis holder disposed within said outer tubular device, said prosthesis holder comprising:
an axial guidewire extending through said prosthesis holder
a body surrounding said axial guidewire, said body comprising at least two generally cylindrical markers aligned in a direction parallel to said axial guidewire and each spaced an equal distance from said axial guidewire; and
an outer surface, upon which a prosthesis may be secured prior to delivery.

Embodiment 2

The delivery system of embodiment 1, wherein said prosthesis holder is made of a material that is not fluorescent or radiopaque.

Embodiment 3

The delivery system of embodiment 1, wherein said axial guidewire is made of a material that is fluorescent or radiopaque.

Embodiment 4

The delivery system of embodiment 1, wherein each of said generally cylindrical markers are made of a material that is fluorescent or radiopaque.

Embodiment 5

The delivery system of embodiment 4, wherein each of said generally cylindrical markers are made of a combination of platinum and iridium.

Embodiment 6

The delivery system of embodiment 1, further comprising a third generally cylindrical marker aligned in a direction parallel to said axial guidewire, wherein each of said generally cylindrical markers is spaced an equal distance from said axial guidewire.

Embodiment 7

The delivery system of embodiment 6, wherein each of said generally cylindrical markers are spaced at about 90° intervals as measured around the axis formed by the axial guidewire.

Embodiment 8

The delivery system of embodiment 7, wherein each of said generally cylindrical markers are made of a material that is fluorescent or radiopaque.

Embodiment 9

The delivery system of embodiment 8, wherein each of said generally cylindrical markers are made of a combination of platinum and iridium.

Embodiment 10

The delivery system of embodiment 1, further comprising at least one perpendicular marker, wherein said perpendicular marker is disposed at a perpendicular angle to the axial guidewire.

Embodiment 11

The delivery system of embodiment 10, wherein said perpendicular marker is made of a material that is fluorescent or radiopaque.

Embodiment 12

The delivery system of embodiment 11, wherein said perpendicular marker is made of a combination of platinum and iridium.

Embodiment 13

The delivery system of embodiment 6, further comprising at least one perpendicular marker, wherein said perpendicular marker is disposed at a perpendicular angle to the axial guidewire.

Embodiment 14

The delivery system of embodiment 13, wherein said perpendicular marker is made of a material that is fluorescent or radiopaque.

Embodiment 15

The delivery system of embodiment 14, wherein said perpendicular marker is made of a combination of platinum and iridium.

Embodiment 16

The delivery system of embodiment 1, wherein said prosthesis is a stent-graft.

Embodiment 17

The delivery system of embodiment 16, wherein said prosthesis holder comprises a plurality of anchors to secure said stent-graft to said outer surface of said prosthesis holder.

Embodiment 18

The delivery system of embodiment 1, wherein said generally cylindrical markers are press-fitted into said body.

Embodiment 19

The delivery system of embodiment 1, wherein said generally cylindrical markers are molded into said body.

Embodiment 20

The delivery system of embodiment 1, wherein said generally cylindrical markers have a diameter of about 0.030 inches.

Embodiment 21

The delivery system of embodiment 1, wherein said axial guidewire has a diameter of about 0.035 inches.

Embodiment 22

The delivery system of embodiment 6, wherein said generally cylindrical markers are press-fitted into said body.

Embodiment 23

The delivery system of embodiment 6, wherein said generally cylindrical markers are molded into said body.

Embodiment 24

The delivery system of embodiment 6, wherein said generally cylindrical markers have a diameter of about 0.010 to about 0.040 inches.

Embodiment 25

The delivery system of embodiment 6, wherein said axial guidewire has a diameter of about 0.010 to about 0.050 inches.

Embodiment 26

The delivery system of embodiment 1, wherein each of said generally cylindrical markers are disposed in said body at a distance of about 0.010 inches to about 0.015 inches from said axial guidewire.

Embodiment 27

The delivery system of embodiment 6, wherein each of said generally cylindrical markers are disposed in said body at a distance of about 0.010 inches to about 0.015 inches from said axial guidewire.

Embodiment 28

A method of delivering a prosthesis within a body lumen, comprising the steps of:
(a) providing a delivery system comprising:
  (i) an elongate outer tubular device having an open lumen and opposed proximal and distal ends with a medial portion therein between; and
  (ii) a prosthesis holder disposed within said outer tubular device, said prosthesis holder comprising:
    an axial guidewire extending through said prosthesis holder
    a body surrounding said axial guidewire, said body comprising at least two generally cylindrical markers aligned in a direction parallel to said axial guidewire and each spaced an equal distance from said axial guidewire;

an outer surface; and
a prosthesis secured to said outer surface;
(b) inserting said delivery system within a body lumen and directing said prosthesis holder to a desired location within the lumen;
(c) using a device to view the location of the generally cylindrical markers;
(d) aligning said prosthesis holder at a rotational angle based upon the generally cylindrical markers; and
(e) releasing said prosthesis within said body lumen.

Embodiment 29

The method of embodiment 28, wherein said prosthesis holder is made of a material that is not fluorescent or radiopaque.

Embodiment 30

The method of embodiment 28, wherein said axial guidewire is made of a material that is fluorescent or radiopaque.

Embodiment 31

The method of embodiment 28, wherein each of said generally cylindrical markers are made of a material that is fluorescent or radiopaque.

Embodiment 32

The method of embodiment 31, wherein each of said generally cylindrical markers are made of a combination of platinum and iridium.

Embodiment 33

The method of embodiment 28, further comprising a third generally cylindrical marker aligned in a direction parallel to said axial guidewire, wherein each of said generally cylindrical markers is spaced an equal distance from said axial guidewire.

Embodiment 34

The method of embodiment 33, wherein each of said generally cylindrical markers are spaced at about 90° intervals as measured around the axis formed by the axial guidewire.

Embodiment 35

The method of embodiment 34, wherein each of said generally cylindrical markers are made of a material that is fluorescent or radiopaque.

Embodiment 36

The method of embodiment 35, wherein each of said generally cylindrical markers are made of a combination of platinum and iridium.

Embodiment 37

The method of embodiment 28, further comprising at least one perpendicular marker, wherein said perpendicular marker is disposed at a perpendicular angle to the axial guidewire.

Embodiment 38

The method of embodiment 37, wherein said perpendicular marker is made of a material that is fluorescent or radiopaque.

Embodiment 37

The method of embodiment 38, wherein said perpendicular marker is made of a combination of platinum and iridium.

Embodiment 38

The method of embodiment 33, further comprising at least one perpendicular marker, wherein said perpendicular marker is disposed at a perpendicular angle to the axial guidewire.

Embodiment 39

The method of embodiment 38, wherein said perpendicular marker is made of a material that is fluorescent or radiopaque.

Embodiment 40

The method of embodiment 39, wherein said perpendicular marker is made of a combination of platinum and iridium.

Embodiment 41

The method of embodiment 28, wherein said prosthesis is a stent-graft.

Embodiment 42

The method of embodiment 41, wherein said prosthesis holder comprises a plurality of anchors to secure said stent-graft to said outer surface of said prosthesis holder.

Embodiment 43

The method of embodiment 28, wherein said generally cylindrical markers are press-fitted into said body.

Embodiment 44

The method of embodiment 28, wherein said generally cylindrical markers are molded into said body.

Embodiment 45

The method of embodiment 28, wherein said generally cylindrical markers have a diameter of about 0.030 inches.

Embodiment 46

The method of embodiment 28, wherein said axial guidewire has a diameter of about 0.035 inches.

Embodiment 47

The method of embodiment 33, wherein said generally cylindrical markers are press-fitted into said body.

Embodiment 48

The method of embodiment 33, wherein said generally cylindrical markers are molded into said body.

Embodiment 49

The method of embodiment 33, wherein said generally cylindrical markers have a diameter of about 0.030 inches.

Embodiment 50

The method of embodiment 33, wherein said axial guidewire has a diameter of about 0.035 inches.

Embodiment 51

The method of embodiment 28, wherein each of said generally cylindrical markers are disposed in said body at a distance of about 0.010 inches to about 0.015 inches from said axial guidewire.

Embodiment 52

The method of embodiment 33, wherein each of said generally cylindrical markers are disposed in said body at a distance of about 0.010 inches to about 0.015 inches from said axial guidewire.

Embodiment 53

The method of embodiment 28, wherein said device comprises a monitor to view radiographic or fluorescent materials.

Embodiment 54

The method of embodiment 53, wherein said monitor reads an image the lumen of a patient at an angle that is perpendicular to the axis formed by the axial guidewire.

Embodiment 55

The method of embodiment 54, wherein said step (d) of aligning said prosthesis holder at a rotational angle based upon the cylindrical markers comprises the steps of:
(i) viewing said monitor;
(ii) measuring the size of the distance between the generally cylindrical markers and the axial guidewire; and
(iii) rotating said prosthesis holder until the distance between the generally cylindrical markers and axial guidewire is at its largest.

While various embodiments of the present invention are specifically illustrated and/or described herein, it will be appreciated that modifications and variations of the present invention may be effected by those skilled in the art without departing from the spirit and intended scope of the invention. Further, any of the embodiments or aspects of the invention as described in the claims or in the specification may be used with one and another without limitation.

What is claimed is:

1. An endovascular delivery system, comprising:
an elongate outer tubular device having an open lumen and opposed proximal and distal ends with a medial portion therein between;
an inner tubular member disposed within said outer tubular device, said inner tubular member comprising prosthesis holder comprising:
an axial guidewire extending through said proximal portion of said inner tubular member;
a body surrounding said axial guidewire; and
an outer surface, upon which a prosthesis may be secured prior to delivery;
wherein said body comprises:
at least three generally cylindrical markers aligned in a direction parallel to said axial guidewire and each spaced an equal distance from said axial guidewire with one of the cylindrical markers being a middle cylindrical marker and another two of the cylindrical markers being side cylindrical markers; and
at least two perpendicular markers, wherein said perpendicular markers are disposed at a perpendicular angle to the axial guidewire;
wherein each of said generally cylindrical markers are spaced at about 90° intervals as measured around the axis formed by the axial guidewire;
wherein, upon rotation of the proximal portion to a first position, only the middle cylindrical marker and the two perpendicular markers are visible and, upon rotation of the proximal portion to a second position, only the two side cylindrical markers are visible.

2. The delivery system of claim 1, wherein said body is made of a material that is not fluorescent or radiopaque.

3. The delivery system of claim 1, wherein said axial guidewire is made of a material that is fluorescent or radiopaque.

4. The delivery system of claim 1, wherein each of said generally cylindrical markers are made of a material that is fluorescent or radiopaque.

5. The delivery system of claim 4, wherein each of said generally cylindrical markers are made of a combination of platinum and iridium.

6. The delivery system of claim 1, wherein said perpendicular markers are made of a material that is fluorescent or radiopaque.

7. The delivery system of claim 6, wherein said perpendicular markers are made of a combination of platinum and iridium.

8. The delivery system of claim 1, wherein said prosthesis is a stent-graft.

9. The delivery system of claim 8, wherein said body comprises a plurality of anchors to secure said stent-graft to said outer surface of said body.

10. The delivery system of claim 1, wherein said generally cylindrical markers are press-fitted into said body.

11. The delivery system of claim 1, wherein said generally cylindrical markers are molded into said body.

12. The delivery system of claim 1, wherein said generally cylindrical markers have a diameter of about 0.030 inches.

13. The delivery system of claim 1, wherein said axial guidewire has a diameter of about 0.035 inches.

14. The delivery system of claim 1, wherein said generally cylindrical markers have a diameter of about 0.010 to about 0.040 inches.

15. The delivery system of claim 1, wherein said axial guidewire has a diameter of about 0.010 to about 0.050 inches.

16. The delivery system of claim 1, wherein each of said generally cylindrical markers are disposed in said body at a distance of about 0.010 inches to about 0.015 inches from said axial guidewire.

17. A method of delivering a prosthesis within a body lumen, comprising the steps of:
 (a) providing the delivery system of claim 1;
 (b) inserting said delivery system within a body lumen and directing said prosthesis holder to a desired location within the lumen;
 (c) using a device to view the location of the generally cylindrical markers;
 (d) aligning said prosthesis holder at a rotational angle based upon the generally cylindrical markers; and
 (e) releasing said prosthesis within said body lumen.

\* \* \* \* \*